United States Patent
O'Neil et al.

(10) Patent No.: US 9,936,938 B2
(45) Date of Patent: *Apr. 10, 2018

(54) BALLOON WITH SHAPE CONTROL FOR SPINAL PROCEDURES

(71) Applicant: DePuy Synthes Products, Inc., Raynham, MA (US)

(72) Inventors: Michael J. O'Neil, West Barnstable, MA (US); Michael Andrew Slivka, Taunton, MA (US); Anwar M. Upal, Fall River, MA (US); John Riley Hawkins, Cumberland, RI (US); Michael Alan Fisher, Middleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 67 days.

This patent is subject to a terminal disclaimer.

(21) Appl. No.: 15/218,131

(22) Filed: Jul. 25, 2016

(65) Prior Publication Data

US 2016/0331362 A1    Nov. 17, 2016

Related U.S. Application Data

(63) Continuation of application No. 14/925,615, filed on Oct. 28, 2015, now Pat. No. 9,421,056, which is a
(Continued)

(51) Int. Cl.
*A61M 29/00* (2006.01)
*A61B 17/02* (2006.01)
(Continued)

(52) U.S. Cl.
CPC ........ *A61B 17/025* (2013.01); *A61B 17/8805* (2013.01); *A61F 2/442* (2013.01); *A61M 29/02* (2013.01); *A61B 2017/00557* (2013.01); *A61B 2017/0225* (2013.01); *A61B 2017/0256* (2013.01); *A61M 25/1002* (2013.01); *A61M 2025/1063* (2013.01)

(58) Field of Classification Search
CPC .............. A61B 17/025; A61B 17/8805; A61B 2017/0225; A61B 2017/00557; A61B 2017/0256; A61B 17/8802; A61B 17/8811; A61B 17/885; A61B 17/8852; A61B 17/8855; A61B 17/8858; A61B 17/00082; A61B 2017/320048; A61F 2/442; A61F 2/441; A61F 2/44; A61M 29/02; A61M 2025/1063; A61M 25/1002; A61M 25/10
USPC ..... 623/17.11–17.19; 606/90, 192–193, 197; 600/207
See application file for complete search history.

(56) References Cited

U.S. PATENT DOCUMENTS 4,863,476 A    9/1989  Shepperd
5,163,949 A *  11/1992 Bonutti .............. A61B 17/0218
                                               606/192
(Continued)

FOREIGN PATENT DOCUMENTS

WO          00/74605 A1    12/2000

*Primary Examiner* — Amy R Weisberg
(74) *Attorney, Agent, or Firm* — Nutter McClennen & Fish LLP

(57) ABSTRACT

In intervertebral operative spinal procedures, using separate or pre-attached spreader blocks to control the directional growth of a distracting balloon.

19 Claims, 21 Drawing Sheets

Related U.S. Application Data continuation of application No. 11/863,839, filed on Sep. 28, 2007, now abandoned.

(51) Int. Cl.
*A61M 29/02* (2006.01)
*A61B 17/88* (2006.01)
*A61F 2/44* (2006.01)
*A61M 25/10* (2013.01)
*A61B 17/00* (2006.01)

(56) References Cited

U.S. PATENT DOCUMENTS

| | | | |
|---|---|---|---|
| 5,304,141 A * | 4/1994 | Johnson | A61M 25/0102 604/158 |
| 5,374,267 A | 12/1994 | Siegal | |
| 5,522,899 A | 6/1996 | Michelson | |
| 5,665,122 A | 9/1997 | Kambin | |
| 5,830,188 A * | 11/1998 | Abouleish | A61B 17/3401 604/158 |
| 5,865,848 A | 2/1999 | Baker | |
| 6,030,406 A | 2/2000 | Davis et al. | |
| 6,045,579 A | 4/2000 | Hochshuler et al. | |
| 6,126,689 A | 10/2000 | Brett | |
| 6,176,882 B1 | 1/2001 | Biedermann et al. | |
| 6,248,110 B1 * | 6/2001 | Reiley | A61B 10/025 606/192 |
| 6,254,598 B1 * | 7/2001 | Edwards | A61B 18/1206 606/41 |
| 6,332,894 B1 | 12/2001 | Stalcup et al. | |
| 6,387,130 B1 | 5/2002 | Stone et al. | |
| 6,413,278 B1 | 7/2002 | Marchosky | |
| 6,547,776 B1 * | 4/2003 | Gaiser | A61M 29/02 604/103.02 |
| 6,558,386 B1 * | 5/2003 | Cragg | A61B 17/1642 606/279 |
| 6,595,998 B2 | 7/2003 | Johnson et al. | |
| 6,607,544 B1 * | 8/2003 | Boucher | A61B 17/7097 604/96.01 |
| 6,632,235 B2 | 10/2003 | Weikel et al. | |
| 6,706,069 B2 | 3/2004 | Berger | |
| 6,733,535 B2 | 5/2004 | Michelson | |
| 6,835,208 B2 | 12/2004 | Marchosky | |
| 7,326,248 B2 | 2/2008 | Michelson | |
| 7,452,351 B2 | 11/2008 | Miller et al. | |
| 7,503,920 B2 | 3/2009 | Siegal | |
| 7,632,294 B2 | 12/2009 | Milbodker et al. | |
| 7,655,010 B2 | 2/2010 | Serhan et al. | |
| 7,666,226 B2 | 2/2010 | Schaller | |
| 7,670,374 B2 | 3/2010 | Schaller | |
| 7,703,727 B2 | 4/2010 | Selness | |
| 7,713,273 B2 * | 5/2010 | Krueger | A61B 17/8811 606/92 |
| 7,731,751 B2 | 6/2010 | Butler et al. | |
| 7,785,368 B2 | 8/2010 | Schaller | |
| 7,799,035 B2 * | 9/2010 | Krueger | A61B 17/8819 606/92 |
| 7,799,081 B2 | 9/2010 | McKinley | |
| 7,824,431 B2 * | 11/2010 | McCormack | A61B 17/562 606/279 |
| 7,837,734 B2 | 11/2010 | Zucherman et al. | |
| 7,850,733 B2 | 12/2010 | Baynham et al. | |
| 7,918,874 B2 | 4/2011 | Siegal | |
| 7,942,903 B2 | 5/2011 | Moskowitz et al. | |
| 7,947,078 B2 | 5/2011 | Siegal | |
| 8,007,535 B2 | 8/2011 | Hudgins et al. | |
| 8,034,110 B2 | 10/2011 | Garner et al. | |
| 8,057,544 B2 | 11/2011 | Schaller | |
| 8,088,119 B2 * | 1/2012 | Saal | A61B 17/3401 604/158 |
| 8,105,382 B2 | 1/2012 | Olmos et al. | |
| 8,133,279 B2 * | 3/2012 | Trieu | A61B 17/7097 623/17.11 |
| 8,206,423 B2 | 6/2012 | Siegal | |
| 8,236,029 B2 | 8/2012 | Siegal | |
| 8,241,328 B2 | 8/2012 | Siegal | |
| 8,246,622 B2 | 8/2012 | Siegal et al. | |
| 8,262,666 B2 | 9/2012 | Baynham et al. | |
| 8,267,939 B2 | 9/2012 | Cipoletti et al. | |
| 8,328,812 B2 | 12/2012 | Siegal et al. | |
| 8,343,193 B2 | 1/2013 | Johnson et al. | |
| 8,366,777 B2 | 2/2013 | Matthis et al. | |
| 8,403,990 B2 | 3/2013 | Dryer et al. | |
| 8,414,587 B2 * | 4/2013 | Saal | A61B 17/320783 606/84 |
| 8,425,507 B2 * | 4/2013 | Pellegrino | A61B 17/3472 606/41 |
| 8,454,617 B2 | 6/2013 | Schaller et al. | |
| 8,465,524 B2 | 6/2013 | Siegal | |
| 8,486,109 B2 | 7/2013 | Siegal | |
| 8,579,981 B2 | 11/2013 | Lim et al. | |
| 8,597,330 B2 | 12/2013 | Siegal | |
| 8,672,977 B2 | 3/2014 | Siegal et al. | |
| 8,777,993 B2 | 7/2014 | Siegal et al. | |
| 8,827,981 B2 * | 9/2014 | Liu | A61B 17/8811 604/506 |
| 8,845,638 B2 | 9/2014 | Siegal et al. | |
| 8,894,658 B2 * | 11/2014 | Linderman | A61B 17/8805 606/86 R |
| 8,900,235 B2 | 12/2014 | Siegal | |
| 8,906,098 B2 | 12/2014 | Siegal | |
| 8,961,609 B2 | 2/2015 | Schaller | |
| 8,968,408 B2 | 3/2015 | Schaller et al. | |
| 8,986,388 B2 | 3/2015 | Siegal et al. | |
| 9,017,408 B2 | 4/2015 | Siegal et al. | |
| 9,017,413 B2 | 4/2015 | Siegal et al. | |
| 9,044,334 B2 | 6/2015 | Siegal et al. | |
| 9,095,393 B2 * | 8/2015 | Schaus | A61B 17/8805 |
| 9,126,023 B1 * | 9/2015 | Sahatjian | A61M 25/10 |
| 9,149,612 B2 * | 10/2015 | Chuter | A61M 25/1027 |
| 9,241,806 B2 * | 1/2016 | Suh | A61B 17/8625 |
| 9,254,138 B2 | 2/2016 | Siegal et al. | |
| 9,283,092 B2 | 3/2016 | Siegal et al. | |
| 9,408,712 B2 | 8/2016 | Siegal et al. | |
| 9,421,056 B2 | 8/2016 | O'Neil et al. | |
| 2003/0028251 A1 * | 2/2003 | Mathews | A61B 17/025 623/17.16 |
| 2003/0135275 A1 | 7/2003 | Garcia et al. | |
| 2003/0139812 A1 | 7/2003 | Garcia et al. | |
| 2003/0199979 A1 * | 10/2003 | McGuckin, Jr. | A61B 17/70 623/17.11 |
| 2003/0220649 A1 * | 11/2003 | Bao | A61B 17/7097 606/90 |
| 2004/0002761 A1 | 1/2004 | Rogers et al. | |
| 2004/0073213 A1 | 4/2004 | Serhan et al. | |
| 2004/0087947 A1 | 5/2004 | Lim et al. | |
| 2004/0102774 A1 * | 5/2004 | Trieu | A61B 17/7097 606/86 A |
| 2004/0162559 A1 * | 8/2004 | Arramon | A61B 17/3417 606/62 |
| 2004/0230309 A1 * | 11/2004 | DiMauro | A61F 2/28 623/17.12 |
| 2005/0070900 A1 * | 3/2005 | Serhan | A61B 17/3468 623/17.12 |
| 2005/0070913 A1 * | 3/2005 | Milbocker | A61B 17/00491 606/92 |
| 2005/0090846 A1 * | 4/2005 | Pedersen | A61B 17/22 606/159 |
| 2005/0090852 A1 | 4/2005 | Layne et al. | |
| 2005/0119752 A1 | 6/2005 | Williams et al. | |
| 2005/0288678 A1 * | 12/2005 | Reiley | A61B 17/8855 606/93 |
| 2006/0036241 A1 | 2/2006 | Siegal | |
| 2006/0064101 A1 * | 3/2006 | Arramon | A61B 17/32002 606/82 |
| 2006/0085070 A1 * | 4/2006 | Kim | A61B 17/7065 623/17.11 |
| 2006/0122701 A1 | 6/2006 | Kiester | |
| 2006/0142858 A1 | 6/2006 | Colleran et al. | |
| 2006/0235426 A1 | 10/2006 | Lim et al. | |
| 2006/0264945 A1 | 11/2006 | Edidin et al. | |

(56) References Cited

U.S. PATENT DOCUMENTS

| | | | |
|---|---|---|---|
| 2006/0265076 A1* | 11/2006 | Carter | A61F 2/441 623/17.16 |
| 2007/0010846 A1* | 1/2007 | Leung | A61B 17/3478 606/192 |
| 2007/0010848 A1 | 1/2007 | Leung et al. | |
| 2007/0055272 A1 | 3/2007 | Schaller | |
| 2007/0083225 A1* | 4/2007 | Kiser | A61B 17/29 606/192 |
| 2007/0093901 A1 | 4/2007 | Grotz et al. | |
| 2007/0173785 A1* | 7/2007 | Ostroot | A61M 25/1002 604/509 |
| 2007/0276491 A1* | 11/2007 | Ahrens | A61F 2/441 623/17.11 |
| 2008/0108940 A1* | 5/2008 | Sharkey | A61M 25/0133 604/44 |
| 2008/0133012 A1* | 6/2008 | McGuckin | A61F 2/441 623/17.12 |
| 2008/0161927 A1 | 7/2008 | Savage et al. | |
| 2008/0269756 A1* | 10/2008 | Tomko | A61B 17/1757 606/87 |
| 2009/0076610 A1* | 3/2009 | Afzal | A61F 2/442 623/17.16 |
| 2009/0088789 A1* | 4/2009 | O'Neil | A61M 29/02 606/192 |
| 2009/0234457 A1* | 9/2009 | Lotz | A61F 2/441 623/17.16 |
| 2009/0292287 A1* | 11/2009 | Cragg | A61B 17/1617 606/79 |
| 2010/0010530 A1* | 1/2010 | Rhee | A61F 2/26 606/192 |
| 2010/0137923 A1* | 6/2010 | Greenhalgh | A61B 17/7097 606/86 R |
| 2010/0152792 A1* | 6/2010 | Ralph | A61F 2/442 606/86 A |
| 2010/0168858 A1* | 7/2010 | Hardenbrook | A61B 17/1671 623/17.12 |
| 2010/0274188 A1* | 10/2010 | Chang | A61B 1/227 604/96.01 |
| 2010/0286782 A1* | 11/2010 | Schaller | A61B 17/1642 623/17.12 |
| 2012/0310352 A1 | 12/2012 | DiMauro et al. | |
| 2013/0190875 A1 | 7/2013 | Shulock et al. | |
| 2013/0310943 A1* | 11/2013 | McCormack | A61B 17/025 623/17.16 |
| 2014/0052259 A1 | 2/2014 | Garner et al. | |
| 2014/0257239 A1* | 9/2014 | Arthur | A61B 17/8855 604/506 |
| 2014/0277467 A1* | 9/2014 | Hibri | A61F 2/44 623/17.12 |
| 2015/0230932 A1* | 8/2015 | Schaller | A61F 2/442 623/17.12 |
| 2016/0045240 A1 | 2/2016 | O'Neil et al. | |

* cited by examiner

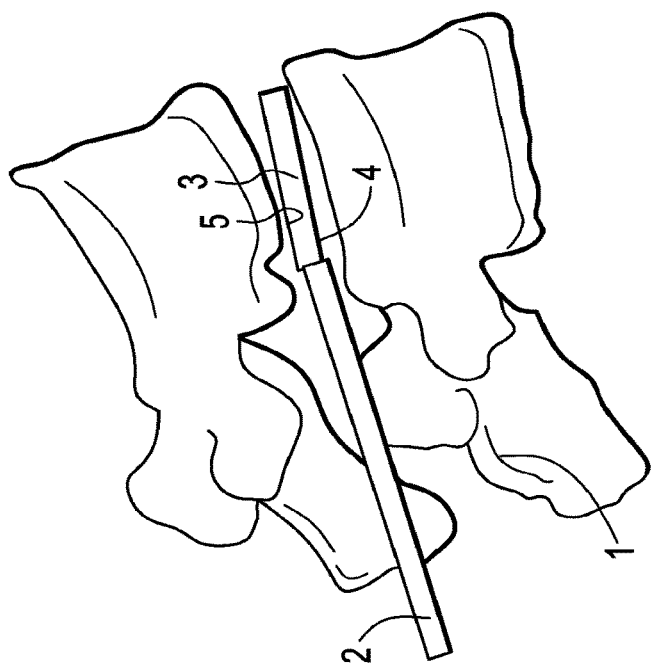
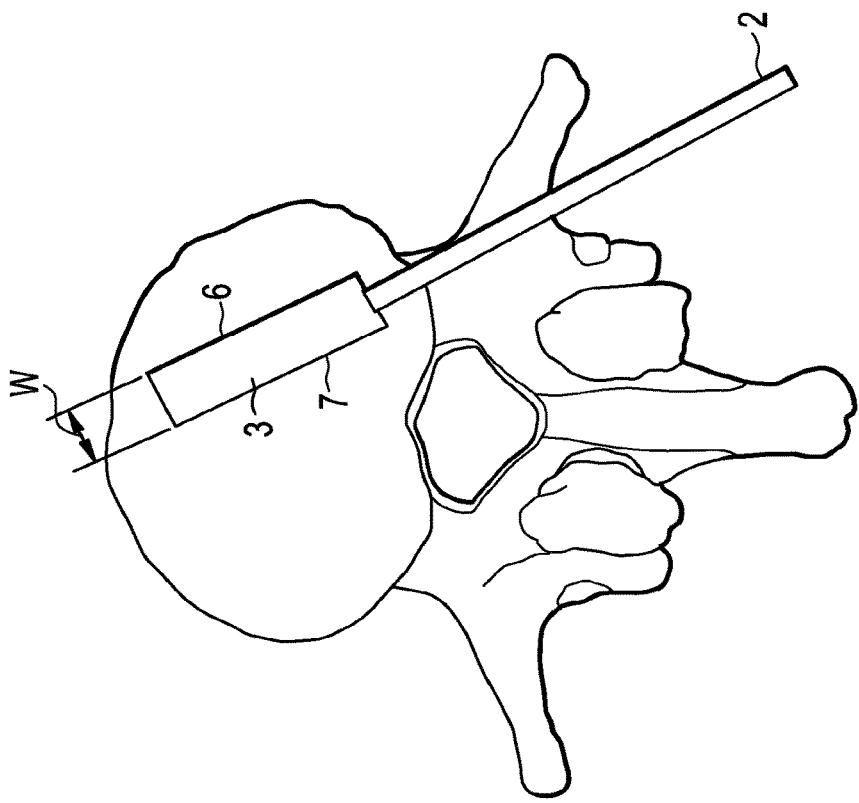

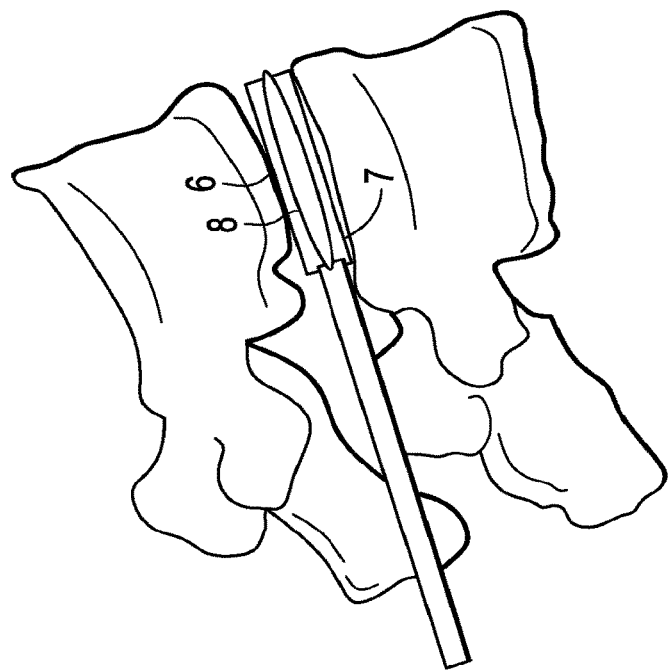
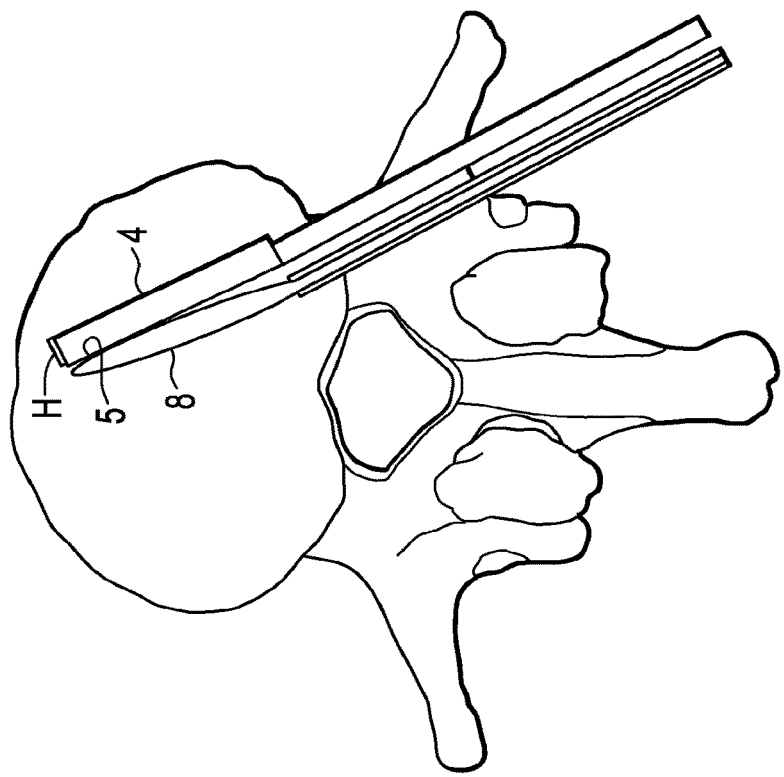

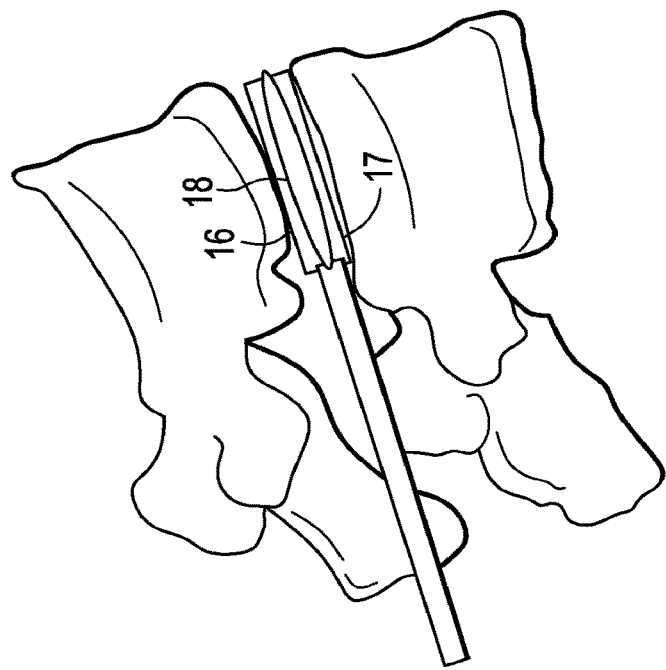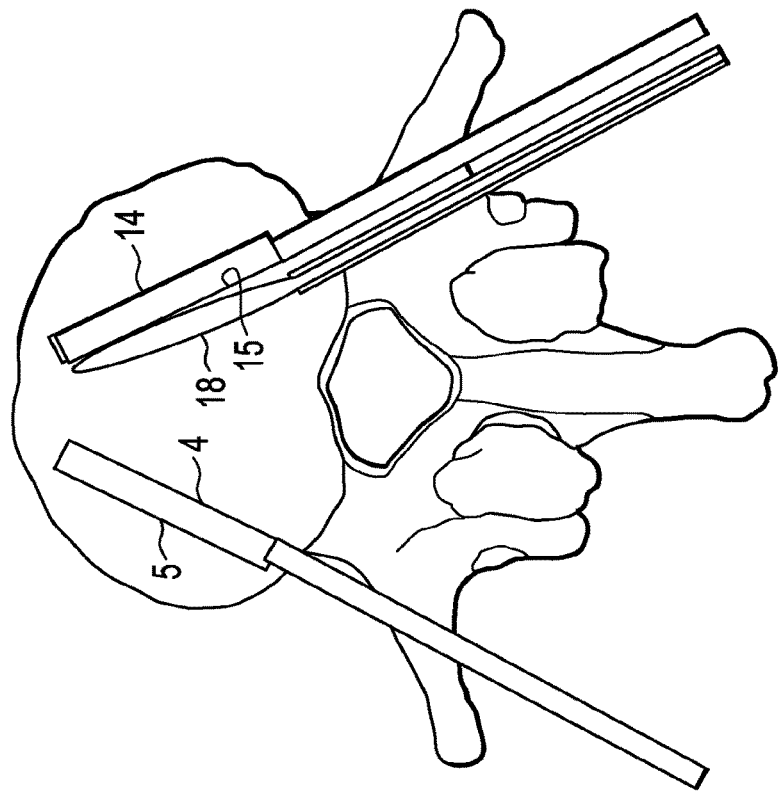

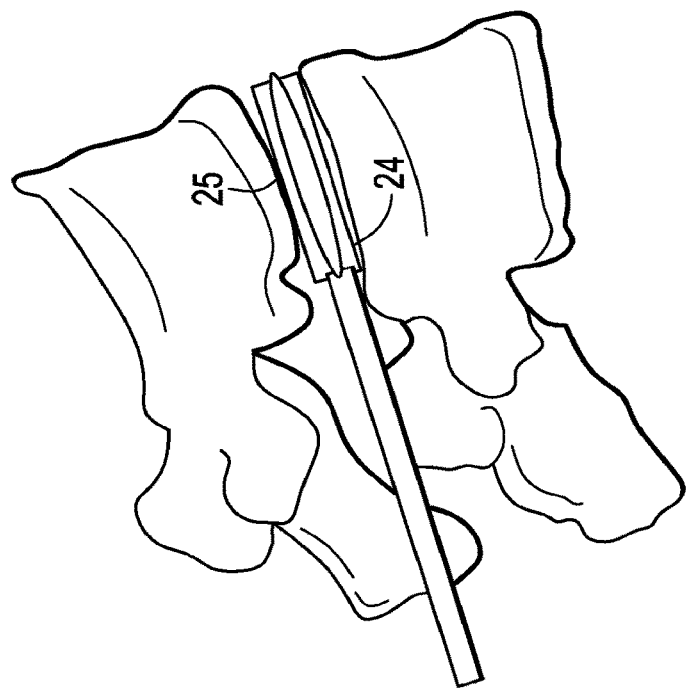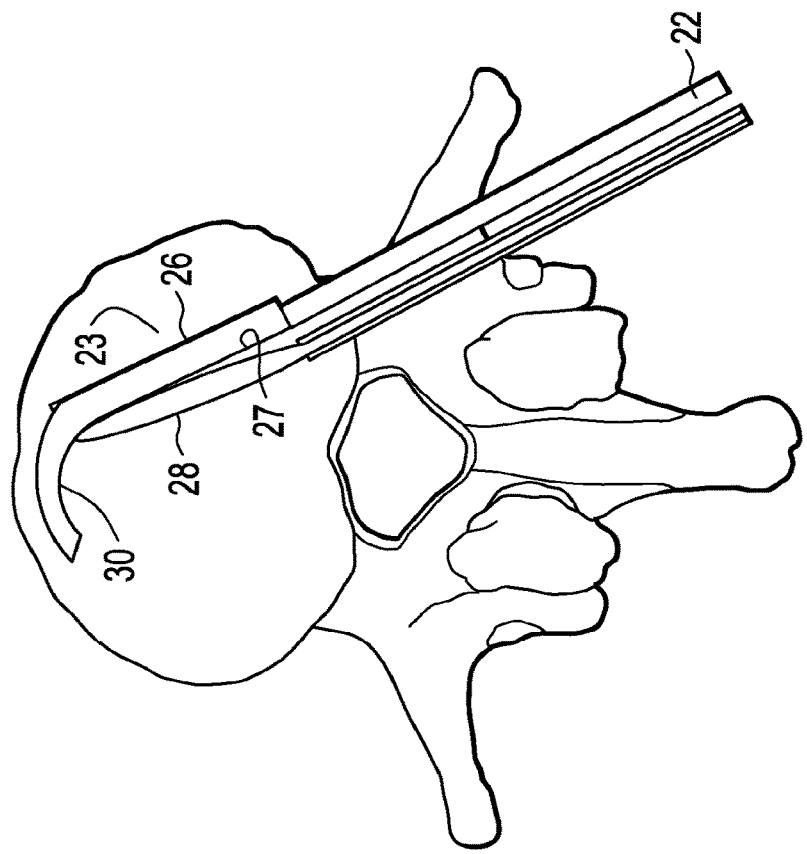

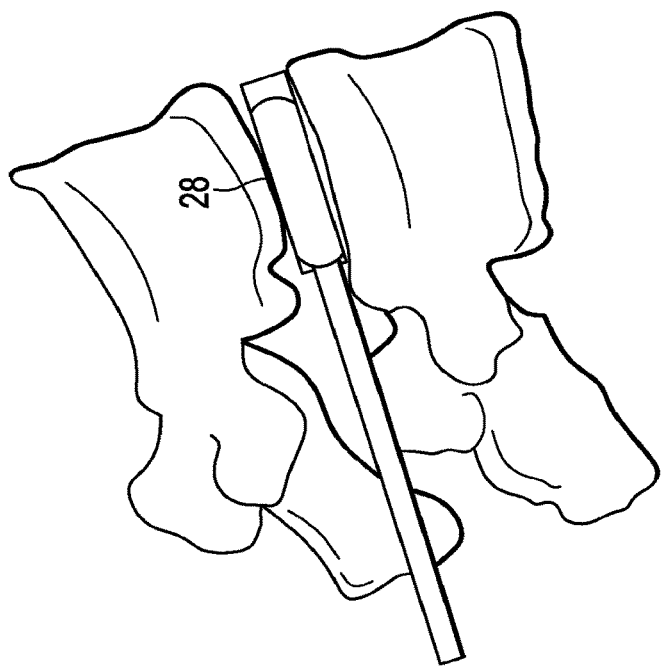
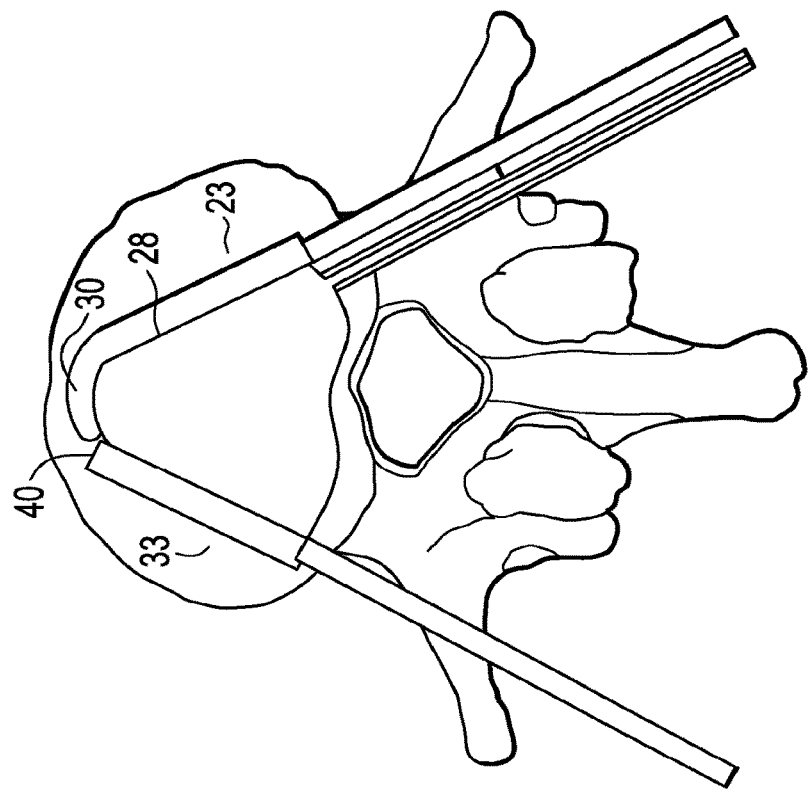
FIG. 10A
FIG. 10B

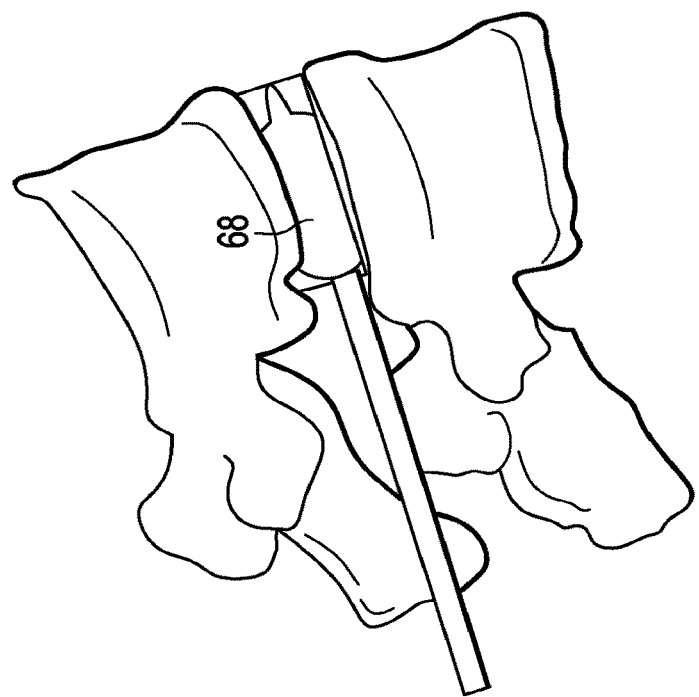
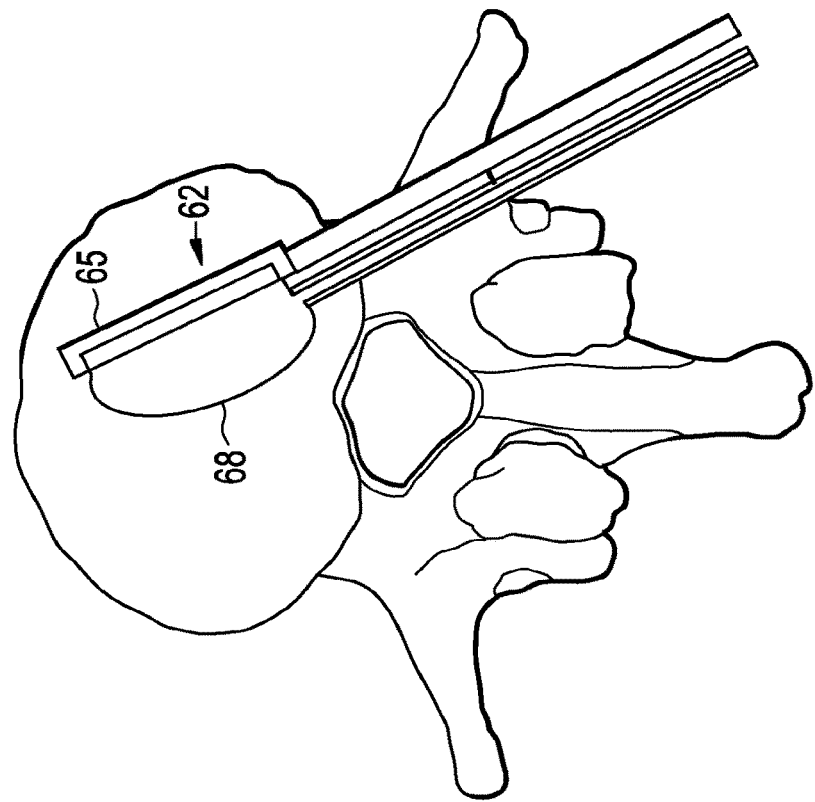

BALLOON WITH SHAPE CONTROL FOR SPINAL PROCEDURES

CROSS-REFERENCE TO RELATED APPLICATIONS

This application is a continuation of U.S. patent application Ser. No. 14/925,615 filed on Oct. 28, 2015, now U.S. Pat. No. 9,421,056, and entitled "Balloon With Shape Control For Spinal Procedures," which is a continuation of U.S. patent application Ser. No. 11/863,839 filed on Sep. 28, 2007, abandoned, and entitled "Balloon With Shape Control For Spinal Procedures," each of which is hereby incorporated herein by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). The cytokines help regulate the metabolism of the nucleus pulposus cells.

In some instances of disc degeneration disease (DDD), gradual degeneration of the intervertebral disc is caused by mechanical instabilities in other portions of the spine. In these instances, increased or unconventional loads and pressures on the nucleus pulposus cause the cells to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins which leads to nerve irritation and pain.

As DDD progresses, the toxic levels of the cytokines present in the nucleus pulposus begin to degrade the extracellular matrix. In particular, the MPPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, and thereby typically upregulating MMPs. As this destructive cascade continues and DDD further progresses, the disc begins to bulge ("a herniated disc"), and then ultimately ruptures, causing the nucleus pulposus to contact the spinal cord and produce pain.

Conventional technology for treating such pain includes the replacing the degenerating disc with either a fusion cage or a motion disc. The literature related to such treatments details the use of both spreader blocks and intra-discal balloons within the intradiscal space. Various spreader blocks are frequently utilized to loosen disc tissue, expand/regain disc height, and encourage vertebral body endplate vascularity. General in-situ balloon art also includes stand alone implants and balloons reinforced with bands, fabrics or scaffolds to enable directional growth.

U.S. Pat. No. 6,632,235 (Weikel) discloses a balloon for insertion into the disk space and inflated to distract the vertebrae. The controlled inflation of the balloon may ensure optimum distraction of the vertebrae and facilitate maximum implant height and neural foraminal decompression. If the balloon is to serve as a distraction instrument, a bone or synthetic allograft along with cancellous bone graft or filler material may then be implanted into contralateral disc space. Once the implant and other materials are in the desired position, the balloon may be deflated and removed from the disk space and a second implant of the same height may be inserted into that space. If the balloon is to serve as a spacer for intervertebral body fusion, the balloon may be inflated with a filler material that sets to form an synthetic allograft implant in vivo. Once the implant has been adequately formed, the balloon may be lysed and removed from the disk space. In another example, the inflated balloon is left intact and is separated from the catheter to remain within the disk space as a scaffold for new bone growth. As previously described, a balloon implant also may be resorbed by physiological conditions and expelled from the patient or transformed and remodeled into new bone growth.

U.S. Pat. No. 6,332,894 (Stalcup) discloses an orthopaedic implant for implanting between adjacent vertebrae and a spine, includes a generally annular bag; and a hardened polymer with the bag. The method of fusing adjacent vertebrae in a spine includes the steps of forming an access hole in an annulus of a disc between the adjacent vertebrae; removing the nucleus within the disc to form a cavity surrounded by the annulus; placing a generally annular bag within the cavity; filling the bag with a polymer; injecting bone particles into the cavity surrounded by the annular bag; and hardening the polymer.

US Published Patent Application 2006/0264945 (Edidin) discloses a scaffold configured to be disposed in a bone. The scaffold is configured to move from a first configuration to a second configuration. The scaffold in the second configuration is expanded from the first configuration. A selectively-expandable actuator is configured to be removably disposed within the scaffold. The selectively-expandable actuator is configured to move at least a portion of the scaffold to the second configuration when the selectively-expandable actuator is moved to an expanded configuration. A shape of the selectively-expandable actuator is substantially the same as a shape of the scaffold when the selectively-expandable actuator and the scaffold are in the second configuration. The selectively-expandable actuator configured to be removed from the scaffold when in a collapsed configuration. The scaffold is configured to remain substantially in the second configuration after the scaffold has been expanded by the actuator.

US Published Patent Application US2005/0070900 (Serhan) discloses an intervertebral fusion device includes a body having a proximal portion along a major axis of the body and a distal portion along the major axis, and supporting means at the distal portion. The supporting means supports vertebrae in a distracted position while the vertebrae fuse. At least one of the body and the supporting means has a height distinct from a width, whereby the body or supporting means can distract vertebrae, between which the body or the supporting means has been placed, by rotation of the body or the supporting means about the major axis. A method of fusing vertebrae includes the steps of inserting between two vertebrae an intervertebral fusion device and rotating the body or the supporting means, whereby the vertebrae are supported in a distracted position while the vertebrae fuse. US2004/0073213 (Serhan) discloses a device for distracting two vertebral bodies and delivering a flowable material into the disc space, comprising a body having a proximal portion and a distal portion, the distal portion having a shape adapted to distract, the body also having a longitudinal bore defining a first outlet port in the distal portion, and a first injection port in the proximal portion.

US Published patent applications US2005/0070900 and US2004/0073213 disclose fluid dispensing through a spreader block. These applications require the balloon(s) to be in direct fluid communication with the spreader.

SUMMARY OF THE INVENTION

The general concept of the present invention relates to devices and methods for minimally invasive disc space distraction and implantation to address degenerative disc disease (DDD), HNP, stenosis, or other conditions of a functional spinal unit.

This present invention uses separate or pre-attached spreader blocks to control the directional growth of the distracting balloon. Preferably, fluid communication to the balloon is not achieved through the block. In addition, spreader block material, geometry and surgical placement options are disclosed to ensure directional expansion including vertical growth for increasing disc space height.

Spreader blocks and a balloon of the present invention are used together as either disc distraction instruments and/or implants. Spreader blocks of varying sizes and shapes are employed to contain balloon expansion in various planes. The balloon containment embodiments that are disclosed herein assist in ensuring directional expansion to accomplish vertical growth for increasing disc space height. The various combinations of balloon and spreader blocks concepts can be divided into (a) non-attached and (b) pre-attached or conjoined embodiments.

Unattached Spreader Blocks and Balloons:

In some embodiments, the spreader blocks and balloon are not physically joined together and so are independent.

Single Spreader Block (see FIGS. 1a-3b).

In one example thereof, a single spreader block and a single independent balloon are initially placed within the disc space. The spreader block is rotated to loosen the annulus fibrosus and regain some of the collapsed disc height. The balloon is then inflated, thereby filling the cleared disc cavity defined by the spreader block and the natural annulus and further distracting the disc to regain even more disc height. The spreader block both limits radial expansion of the balloon and thereby encourages vertical balloon expansion.

Multiple Spreader Blocks:

In other examples wherein the spreader blocks and balloon are independent (i.e., not physically joined together), multiple spreader blocks can be employed to control balloon expansion in multiple directions. See FIGS. 4a-6b. Various spreader block geometries can be used to control balloon expansion towards desired directions or into desired locations. For example, in some embodiments (FIGS. 7a-10b), a curved spreader (which is not rotated) is employed to direct balloon expansion away from the anterior and lateral portions of the annulus fibrosus. In other embodiments (FIGS. 11a & 12b), a slotted spreader block directs balloon expansion to a relatively narrow vertical support beam, thereby significantly limiting balloon expansion in the axial plane and enabling increased balloon expansion in the cranial/caudal plane.

Shape Memory Spreader:

In some embodiments, a shape memory insert is provided as a means for containing the expansion of the balloon in the radial plane while allowing free expansion in the cephalad-caudal directions. See FIGS. 13a-f. The shape memory insert can create a curved barrier, or it can lock upon itself, thereby forming a full ring as the sleeve is retracted (or the shape memory insert advanced). In other embodiments, the shape memory insert may be left free to act as a spring allowing some expansion of the balloon in the coronal/saggital plane.

In some shape memory embodiments, there is provided a method of using a shape memory balloon containment instrument in a disc space, comprising the steps of:
 a) inserting an instrument comprising an insert and a sleeve into disc space,
 b) moving the sleeve relative to the insert to expose the insert, and thereby allowing the insert to curve, contact, connect and/or lock upon itself,
 c) inserting a cannula and a balloon contained therein through a guide channel in the insert,
 d) expanding the balloon,
 e) retracting the insert through the sleeve, and
 f) removing the sleeve while allowing the expanded balloon to remain behind.

Integrated Spreaders and Balloons:

In another embodiment, the spreader block may further possess a means of balloon delivery and expansion. In this case, the balloon and spreader block(s) are provided in an integrated (attached) state and inserted into the disc space as an assembly. Such integrated assemblies can be adapted to carry out to several of the previous concepts. For instance, the spreader block can have a pocket or recess to contain the balloon (see FIG. 14a-b and 15a-b). Alternatively (as seen in FIG. 16a-19b), the spreader block functions as an inserter/spacer to enable balloon expansion and a combination of spreader and balloon geometry controls direction of balloon expansion. In these integrated embodiments, after its expansion, the balloon can be disconnected from the spreader with which it is integrated by cutting or twisting, typically at predetermined break-off locations.

In an alternative embodiment, the balloon is contained within a sectioned spreader block. The spreader block is inserted into a cleared, collapsed disc space, and rotated to regain disc height. Then the balloon is filled. As the balloon fills, it deploys outwards from the spreader block. Sections of the spreader block that are temporarily attached to the balloon deploy with the balloon. The function of these deployed sections is to control the expansion of the balloon—if the deployable spreader block sections are hinged to the base of the spreader block, they only allow the balloon to deploy into an arcuate shape (as depicted in FIGS. 20a-21b. Also, the deployed spreader block sections could help prevent the expanding balloon from assuming a circular cross-section, thereby achieving a long, tall, arcuate balloon (rather than a curved hot dog shape). In these embodiments, the balloon could be operated under high pressure (to cause additional disc space distraction) or low pressure (requiring the spreader block to perform the mechanical work). In this alternative embodiment, the final implant would be the filled, cured, deployed balloon strut in a generally arcuate shape.

In another alternative embodiment, the device includes joined balloon ends with a filler mechanism in the middle. Upon filling, this balloon would assume a crescent shape with the narrow ends of the crescent being attached by a "tether" of unfilled balloon material. This embodiment would provide an arcuate, filled balloon but constructed from multiple circular devices. Thus, a high-pressure balloon is constructed that deploys through a spreader block, distracts the disc space, and forms a self-stable implant strut.

In both the independent and intergrated balloon/spreader embodiments, the balloon can be used as an instrument or as an implant. When utilized as an instrument, the balloon is filled with a fluid (such as a gas, liquid or semi-solid (saline, contrast agent, radiopaque gel, etc.,) to confirm the disc space cavity volume via monitoring the injectate volume and shape via intra-operative imaging. In some embodiments, the injectate can then be evacuated from the balloon and an implant inserted in the disc space. In others, the same balloon (or a new balloon) can be filled with an implant-grade material that encourages fusion (bone cements, osteoinductive cements, bone particles, bone substitutes, growth factors, BMP, etc. . . . ) or maintains motion (viscous gels, cureable elastomers, hydrogels, etc. . . . ).

DESCRIPTION OF THE FIGURES

FIGS. 1a-3b disclose the use of a single spreader block and balloon within the disc space.

FIGS. 4a-6b disclose the use of two spreader blocks and a balloon within the disc space to limit radial expansion of the balloon.

FIGS. 7a-8b disclose the use of a single curved spreader block and balloon within the disc space.

FIGS. 9a-10b disclose the use of a curved spreader block, a straight spreader block and a balloon within the disc space to limit radial expansion of the balloon.

FIG. 14a-15b discloses an integrated distractor, wherein the balloon and spreader are attached.

DETAILED DESCRIPTION OF THE INVENTION

Generally, in independent (or "unattached") embodiments, there is generally provided:
a) a spreader insertion instrument comprising a proximal handle and a distal spreader block having a distal end portion, a height defined by first and second surfaces, and a width defined by third and fourth surfaces, and
b) an inflatable device comprising i) a proximal cannula having a proximal end and a distal end, and ii) a distal balloon having a proximal opening attached to the distal end of the cannula.

A first function of the spreader insertion instrument is to provide an initial distraction of the disc space. Typically, the width of the spreader block is greater than its height (i.e., the distance between its third and fourth surfaces exceeds the distance between its first and second surfaces). Accordingly, when the spreader block is inserted into the disc space (so that its first and second surfaces contact the endplates) and then rotated 90 degrees (so that its third and fourth surfaces contact the natural endplates), the distance between the endplates is increased and distraction is achieved.

The primary function of the balloon is to achieve a further distraction of the disc space. This is accomplished by inserting the balloon into the disc space and inflating the balloon. The inflated balloon pushes against the opposed endplates and enables distraction of the disc space. However, because many conventional balloons are not equipped with a directional bias, the typical balloon expands according to its path of least resistance. Since the opposing endplates present significant resistance to balloon expansion, conventional balloon expansion occurs substantially in the radial direction, that is, parallel to the endplates, thereby lessening its potential to desirably distract of the disc space.

Therefore, a second function of the spreader is to constrain the directional expansion of the balloon. Simply, the spreader provides a blocking function that prevents too much radial expansion of the balloon and directs expansion to occur in the vertical direction, which provides the desired distraction.

Figure 3B:
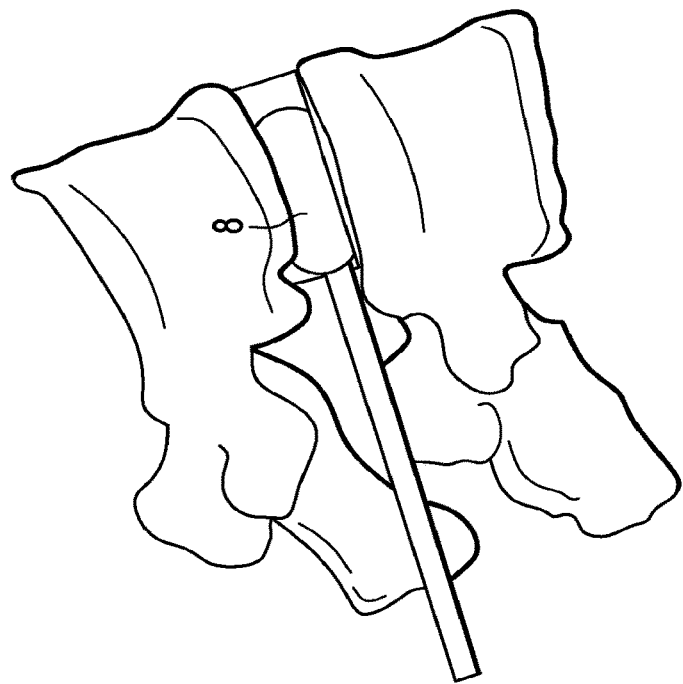
Figure 3A:
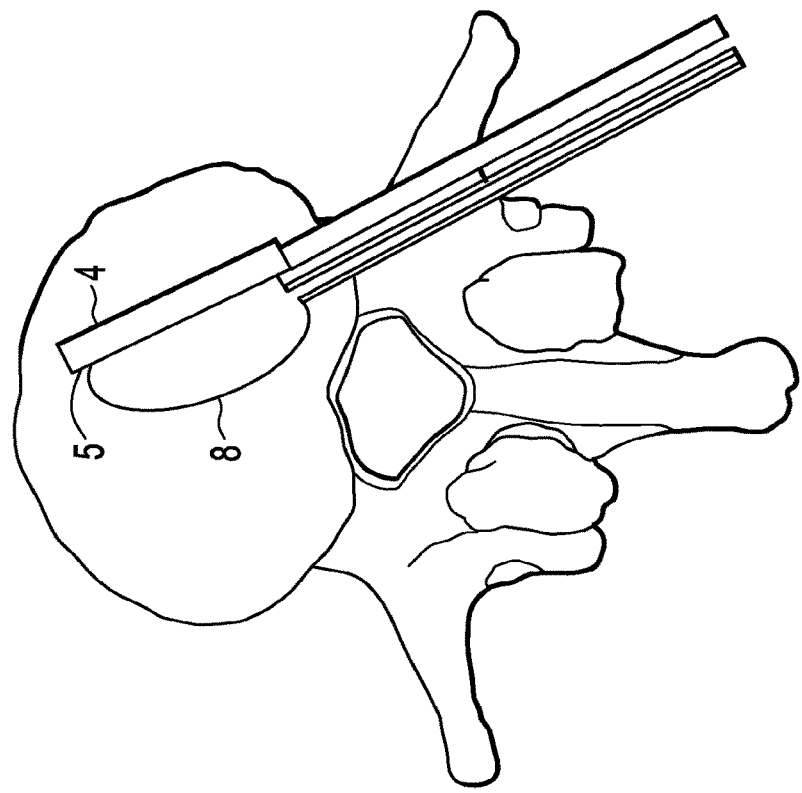

In one embodiment of the present invention, and now referring to FIGS. 1a-3b, there is provided a method of treating a disc, comprising the steps of:
a) providing an insertion instrument 1 comprising a proximal handle 2 and a distal rotatable spreader block 3 having a height H defined by first 4 and second 5 surfaces and a width W defined by third 6 and fourth 7 surfaces,
b) inserting the spreader block into the disc space so that the first and second surfaces thereof contact the opposed vertebral body endplates,
c) rotating the spreader block in the disc space so that the third and fourth surfaces thereof contact the opposed vertebral body endplates,
d) inserting an uninflated balloon 8 into the disc space adjacent the spreader block,
e) inflating the balloon so that the balloon contacts one of the first and second surfaces of the spreader block.

The method disclosed in FIGS. 1a-3b allows the surgeon to sequentially achieve the desired distraction by using an independent balloon and spreader block. The block directs expansion of the balloon in a preferred direction. When the desired distraction is achieved, an intervertebral implant may be inserted into the distracted disc space. After the implant is firmly implanted, the balloon and spreader block may be removed.

Figure 4B:
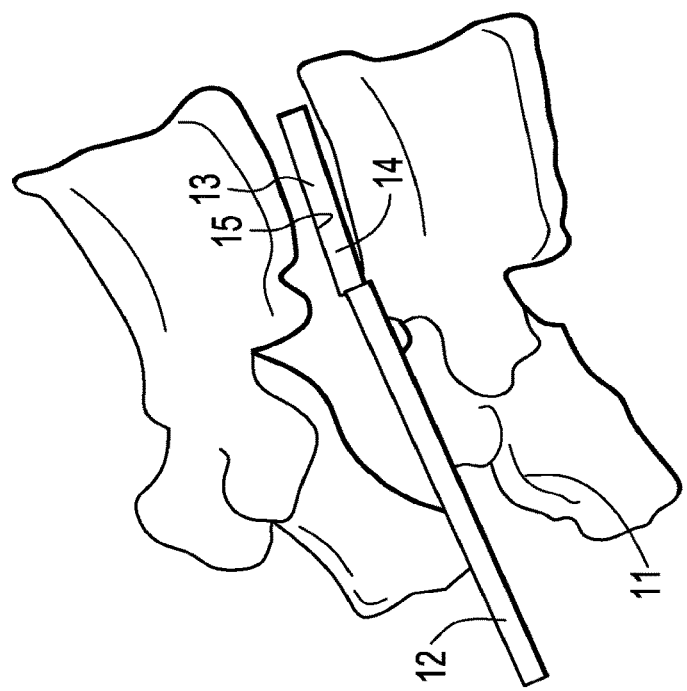
Figure 4A:
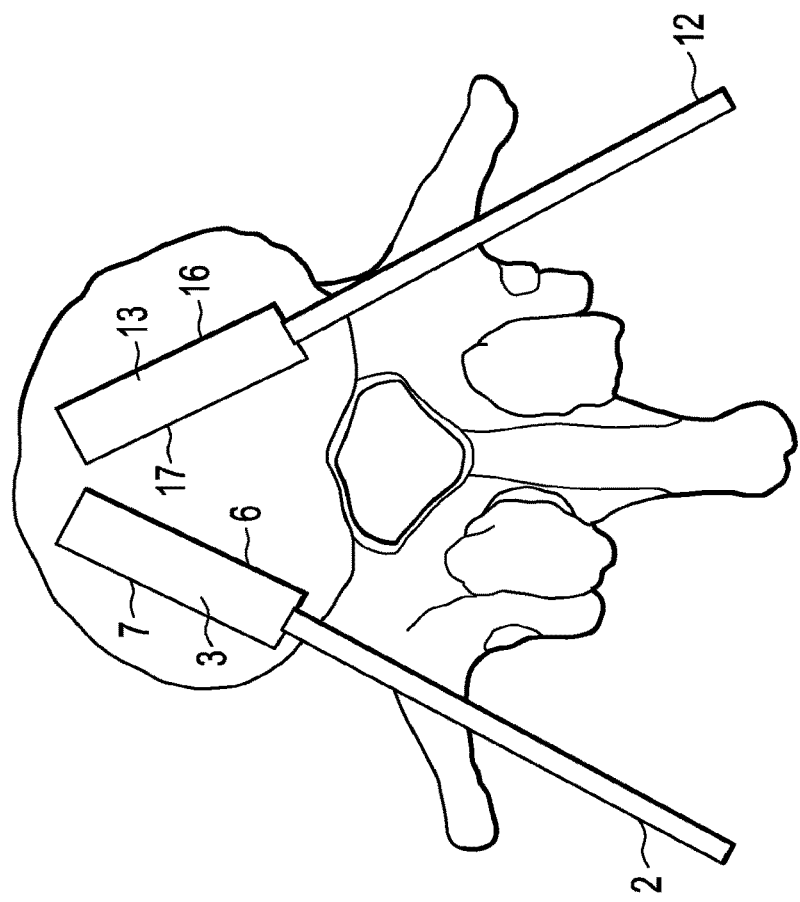
Figure 6B:
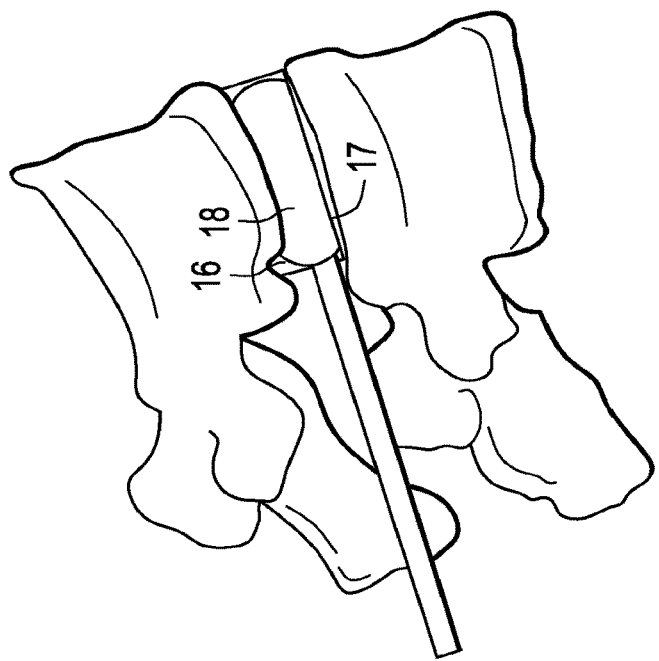
Figure 6A:
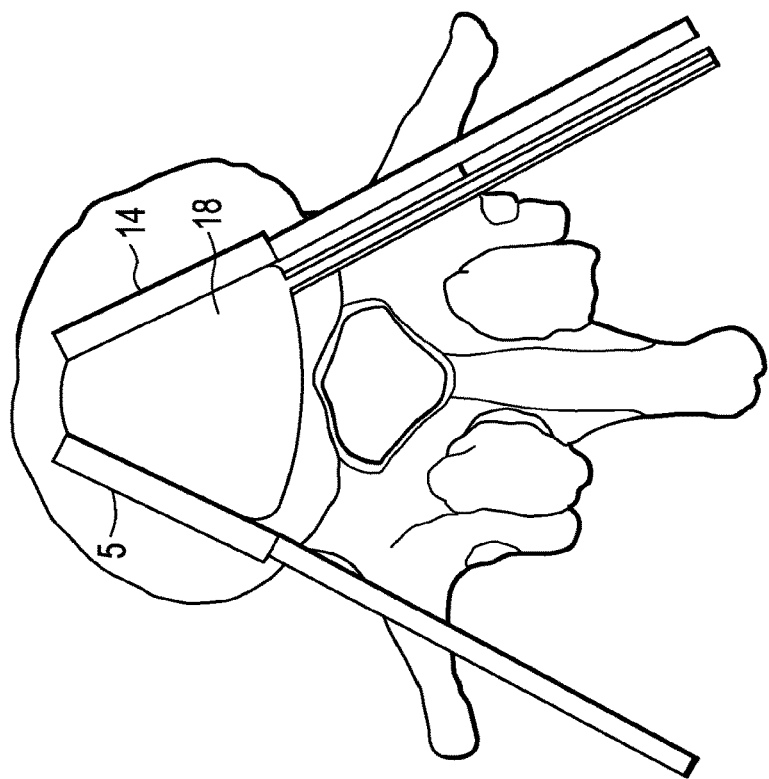

In another embodiment of the present invention, and now referring to FIGS. 4a-6b, there is provided a method of treating a disc, comprising the steps of:
a) providing first 1 and second 11 insertion instruments, each instrument comprising a proximal handle 2,12 and a distal rotatable spreader blocks 3,13, each block having a height defined by first 4,14 and second 5,15 surfaces and a width defined by third 6,16 and fourth 7,17 surfaces,
b) inserting each spreader block into the disc space so that the first and second surfaces thereof contact the opposed vertebral body endplates,
c) rotating each spreader block in the disc space so that the third and fourth surfaces thereof contact the opposed vertebral body endplates,
d) inserting an uninflated balloon 18 into the disc space between the spreader blocks, e) inflating the balloon so that the balloon contacts one of the first and second surfaces of each spreader block.

The method disclosed in FIGS. 4a-6b allows the surgeon to sequentially achieve the desired distraction using an independent balloon and two spreader blocks, wherein the inner surfaces of the opposed spreader blocks define the extremities of radial expansion of the balloon. Thus, the surgeon can control a substantial portion of the footprint made by the balloon in the disc space through the use of a pair of spreader blocks.

Figure 8B:
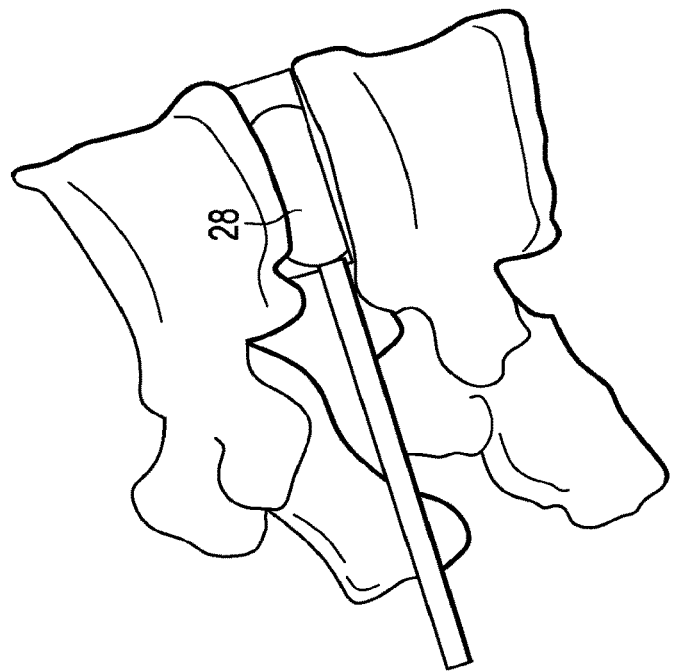
Figure 8A:
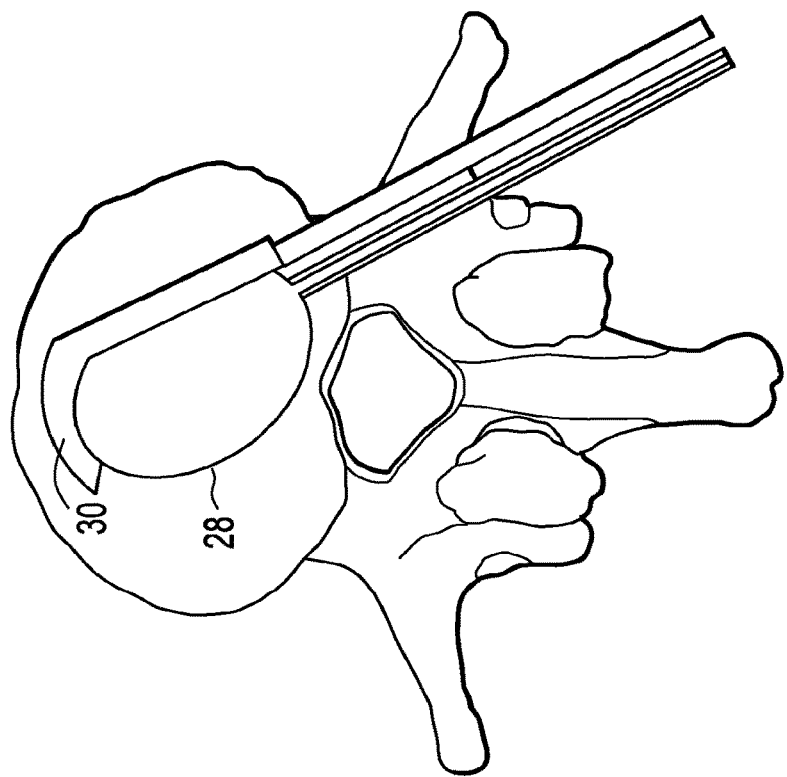

In another embodiment of the present invention, and now referring to FIGS. 7a-8b, there is provided a method of treating a disc, comprising the steps of:
 a) providing an insertion instrument 21 comprising a proximal handle 22 and a distal spreader block 23 having a curved distal end portion 30, a height defined by first 24 and second 25 surfaces and a width defined by third 26 and fourth 27 surfaces,
 b) inserting the spreader block into the disc space so that the first and second surfaces thereof contact the opposed vertebral body endplates,
 c) inserting an uninflated balloon 28 into the disc space adjacent the spreader block,
 d) inflating the balloon so that the balloon contacts the distal end portion of one of the first and second surfaces of the spreader block.

The method disclosed in FIGS. 7a-8b is similar to that of FIGS. 1a-3b in that each allows the surgeon to sequentially achieve the desired distraction using an independent balloon and spreader block. However, in FIGS. 7a-8b, the distal end of the spreader block is curved, thereby constraining the radial expansion of the spreader block.

Figure 9B:
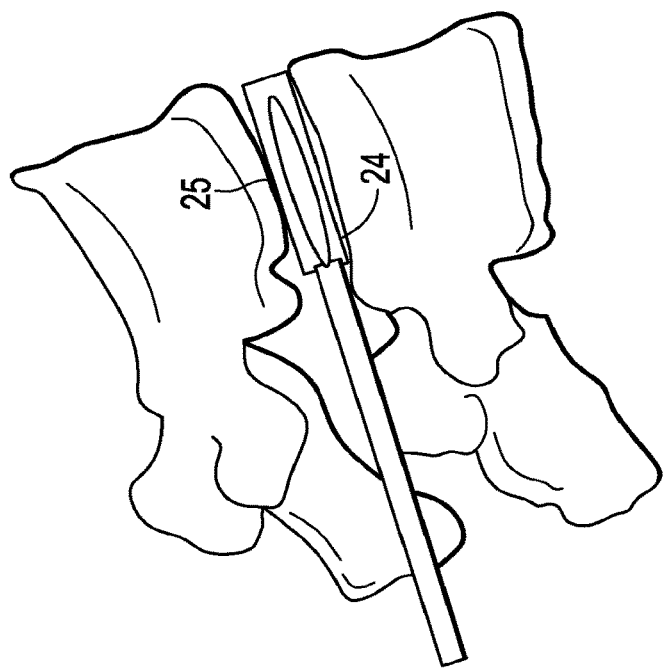
Figure 9A:
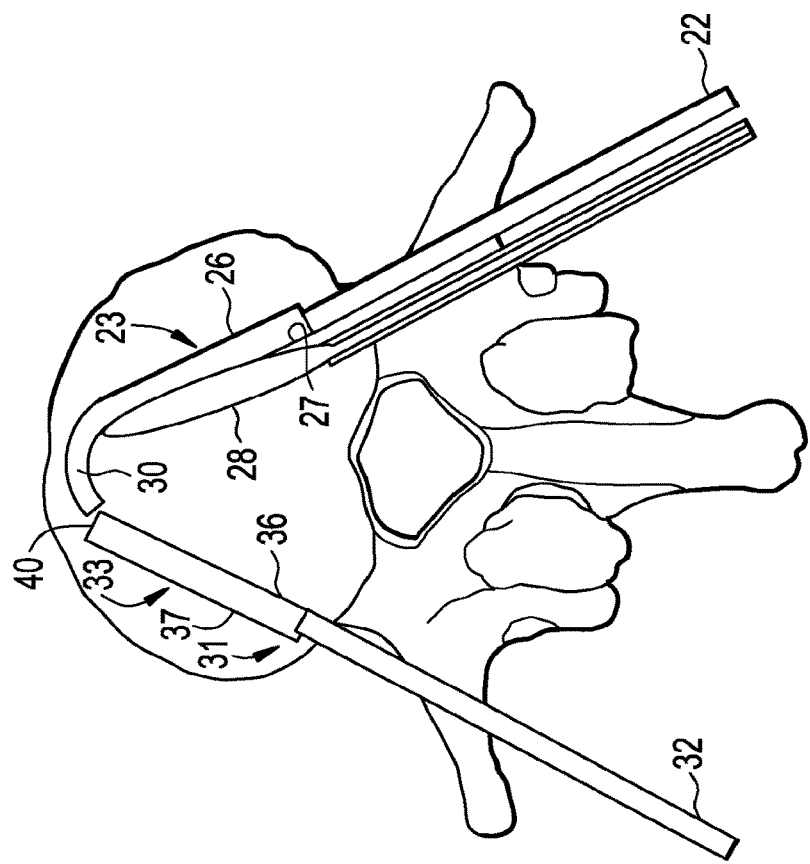

In another embodiment of the present invention, and now referring to FIGS. 9a-10b, there is provided a method of treating a disc, comprising the steps of:
 a) providing a first insertion instrument 21 comprising a proximal handle 22 and a distal spreader block 23 having a curved distal end portion 30, a height defined by first 24 and second 25 surfaces and a width defined by third 26 and fourth 27 surfaces,
 b) providing a second insertion instrument 31 comprising a proximal handle 32 and a distal spreader block 33 having a distal end portion 40, a height defined by first and second surfaces and a width defined by third 36 and fourth 37 surfaces,
 c) inserting each spreader block into the disc space so that the distal end portions are substantially in contact, and the first and second surfaces thereof contact the opposed vertebral body endplates,
 d) inserting an uninflated balloon 28 into the disc space between the spreader blocks,
 e) inflating the balloon so that the balloon contacts the distal end portion of each spreader block.

The method disclosed in FIGS. 9a-10b is similar to that of FIGS. 4a-6b in that each allows the surgeon to sequentially achieve the desired distraction using an independent balloon and two spreader blocks. It is also similar to that of FIGS. 7a-8b, in that the distal end of one spreader block is curved, thereby constraining the radial expansion of the spreader block. Therefore, in this embodiment, the surgeon can control an even greater portion of the footprint made by the balloon in the disc space through the use of a pair of spreader blocks.

Figure 11B:
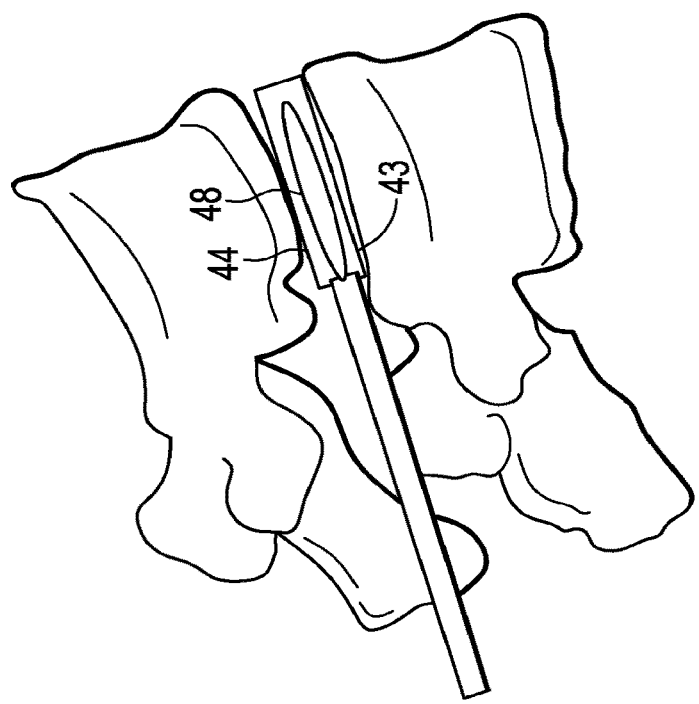
FIGS. 11a-12b disclose the use of a single slotted spreader block and balloon within the disc space.
Figure 11A:
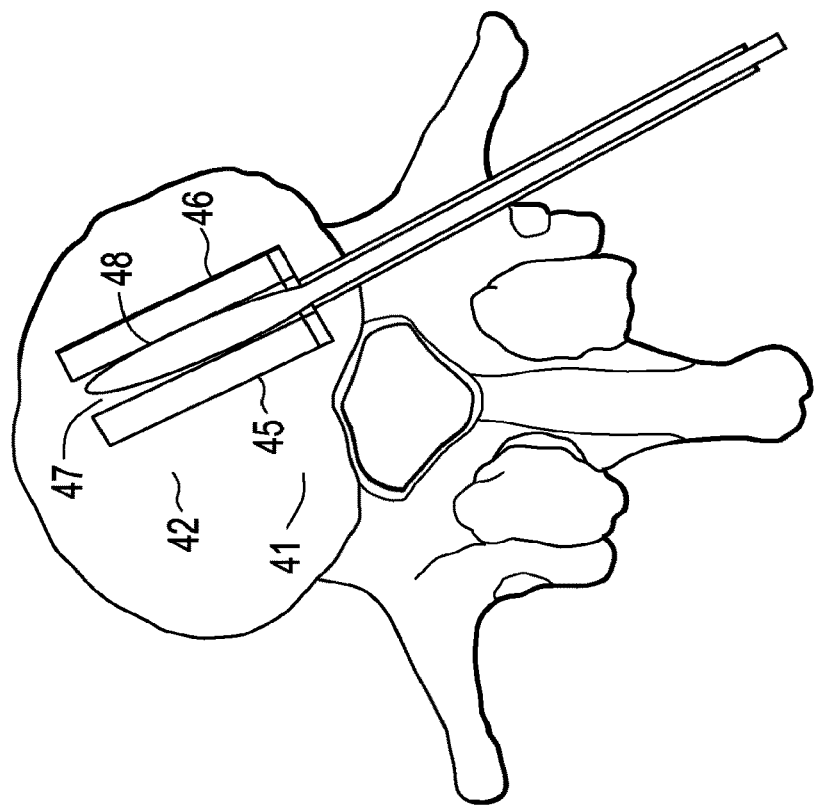
Figure 12B:
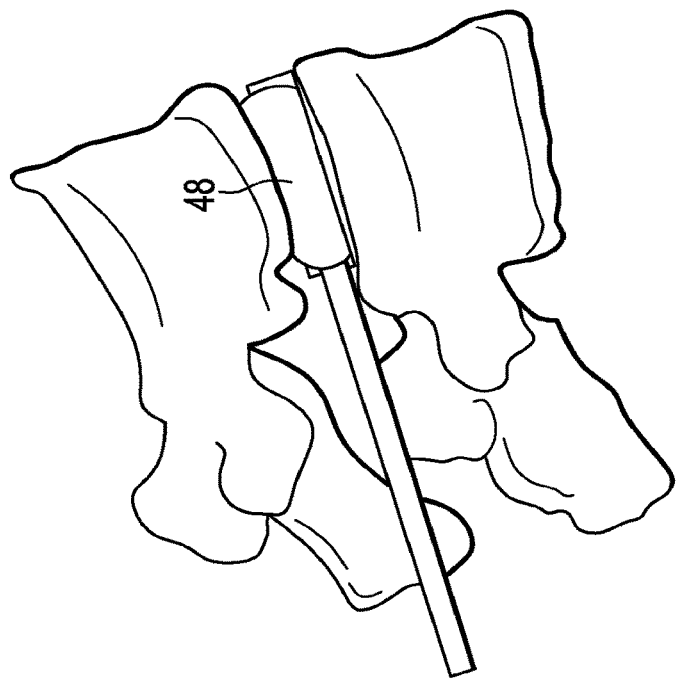
Figure 12A:
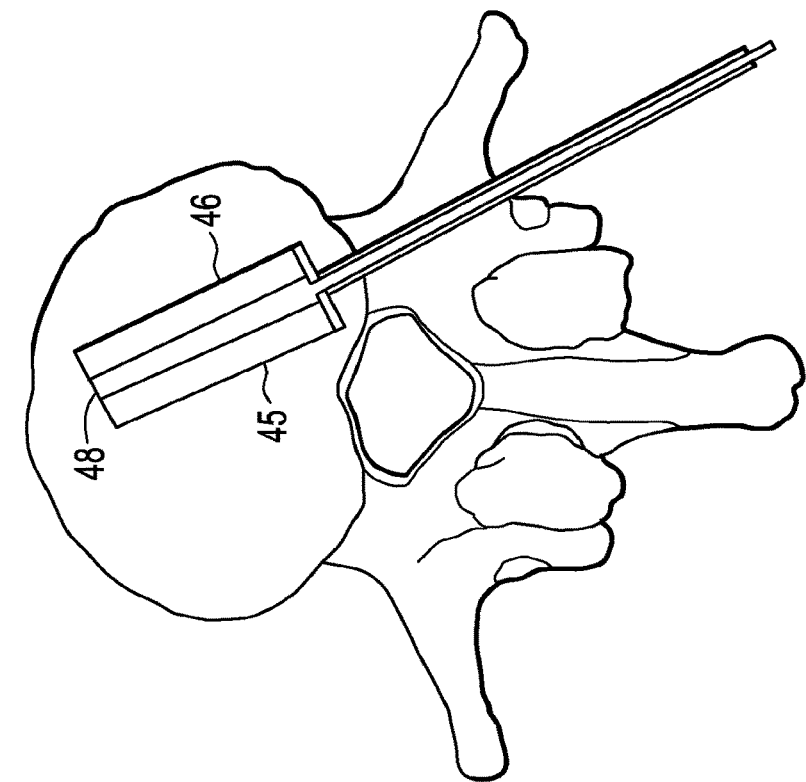

In another embodiment of the present invention, and now referring to FIGS. 11a-12b, there is provided a method of treating a disc, comprising the steps of:
 a) providing an insertion device 41 comprising i) a spreader block 42 having a height defined by first 43 and second 44 surfaces, a width defined by third 45 and fourth 46 surfaces, and a slot 47 extending between the first and second surfaces, and ii) an uninflated balloon 48 within the slot;
 b) inserting the spreader block into the disc space so that the first and second surfaces thereof contact the opposed vertebral body endplates, and
 c) inflating the balloon so that the balloon substantially contacts one of the first and second surfaces of each spreader block.

In this embodiment, the spreader block has a through-slot extending in the vertical direction. The block is inserted into the disc space so that the slot contacts the opposing endplates. Expansion of the balloon occurs through the slot and so occurs substantially in the vertical direction, thereby forcing the endplates apart and creating distraction.

Figure 13A:
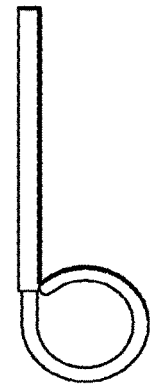
FIG. 13a-f discloses an embodiment utilizing a shape memory structure.
Figure 13B:
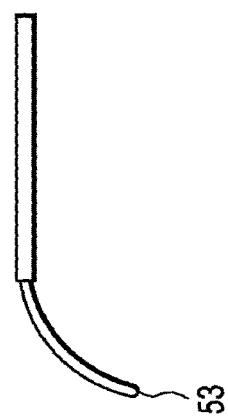
Figure 13C:
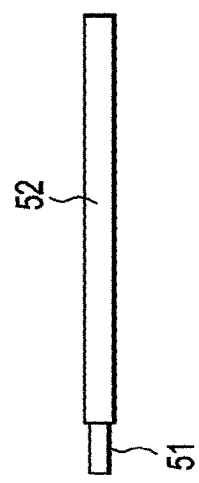
Figure 13D:
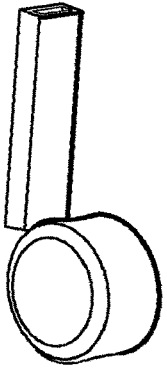
Figure 13E:
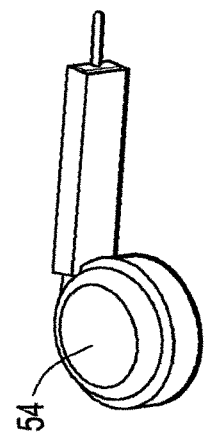
Figure 13F:
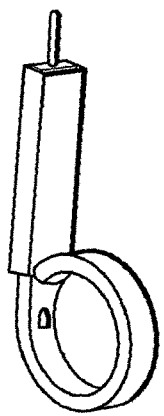

In another embodiment of the present invention, and now referring to FIGS. 13a-13f, there is provided a method of treating a disc, comprising the steps of:
 a) providing a pair of co-axial outer 51 and inner 52 cannulae, wherein the inner cannula has a distal portion 53 comprising a delivery hole and comprises a shape memory material,
 b) inserting the co-axial outer and inner cannulae into the disc space,
 c) moving the outer cannula relative to the inner cannula to expose the inner cannula (for example, retracting the outer cannula), thereby causing the distal portion of the inner shape memory cannula to revert to a memorized annular shape having an inner surface including the delivery hole,
 d) delivering an uninflated balloon 54 to the disc space through the delivery hole of the inner cannula, and
 e) inflating the balloon to substantially contact the inner surface of the memorized annular shape, and
 f) retracting the inner cannula.

In this embodiment, a shape memory insert is provided as a means for containing the expansion of the balloon in the radial plane while allowing free expansion in the cephalad-caudal directions. Once, the balloon shape has been created within the shape memory structure, the balloon may be filled with a curable substance that fixes the shape of the balloon. The shape memory structure may then be withdrawn.

Figure 14B:
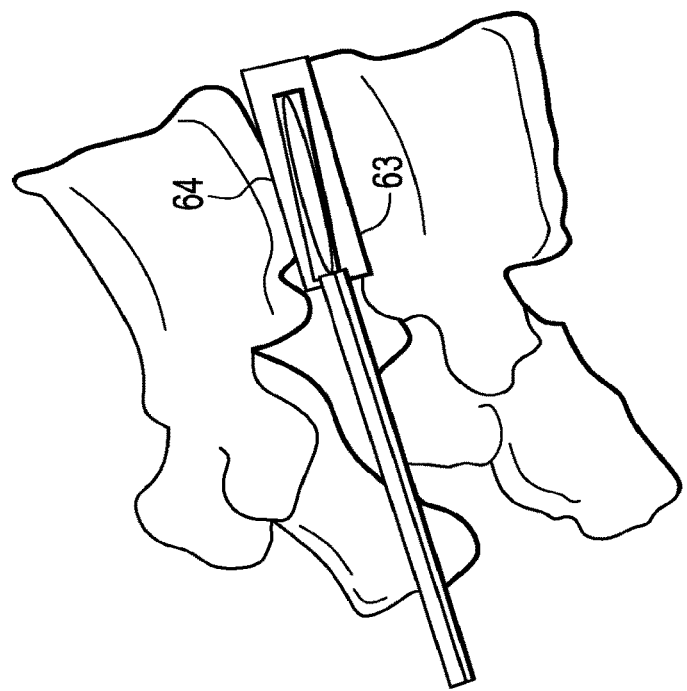
Figure 14A:
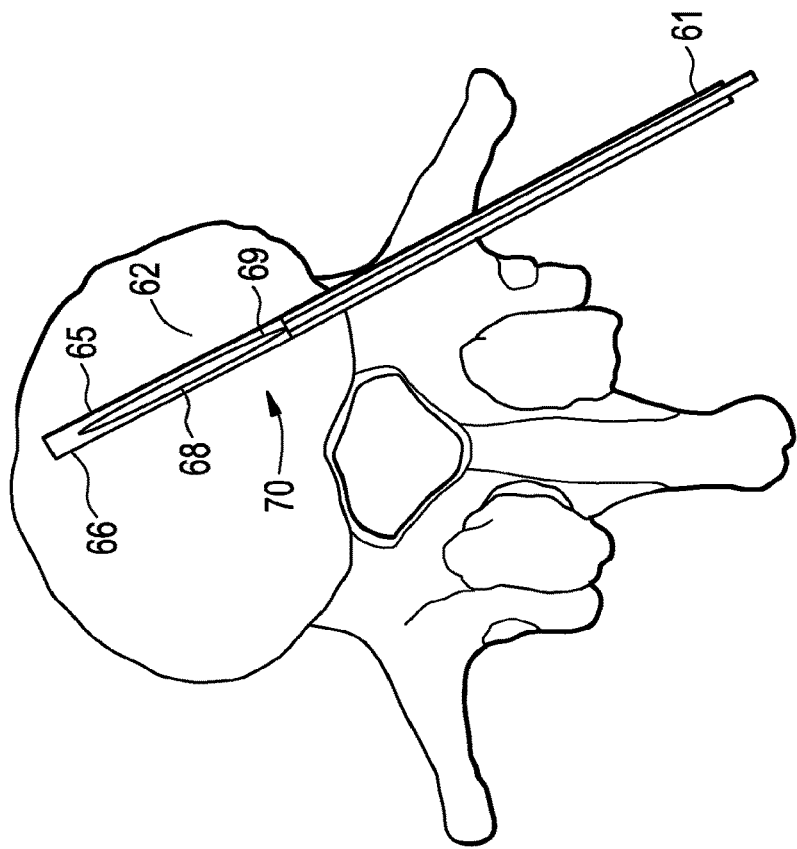

In another embodiment of the present invention, and now referring to FIGS. 14a-15b, there is provided a method of treating a disc, comprising the steps of:
 a) providing an distractor comprising:
  i) a proximal cannulated handle 61 having a through-bore, and
  ii) a distal portion 70 attached to the handle comprising a rotatable spreader block 62 having a height defined by first 63 and second 64 surfaces and a width defined by third 65 and fourth 66 surfaces, and an uninflated balloon 68 having an open end 69 attached to the throughbore and adjacent one of the first and second surfaces of the spreader block,
 b) inserting the distractor into the disc space so that the first and second surfaces thereof contact the opposed vertebral body endplates,
 c) rotating the spreader block in the disc space so that the third and fourth surfaces thereof contact the opposed vertebral body endplates, d) inflating the balloon so that the balloon contacts the opposed vertebral body endplates and is directionally biased by one of the first and second surfaces of the spreader block This method provides for use of an integrated distractor, wherein the balloon and spreader are attached.

Also in accordance with the present invention, and still referring to FIGS. 14a-15b, there is provided a distractor comprising:
- i) a proximal cannulated handle having a throughbore, and
- ii) a distal portion attached to the handle comprising:
   - a rotatable spreader block having a height defined by first and second surfaces and a width defined by third and fourth surfaces, and
   - an uninflated balloon having an open end attached to the throughbore.

In some embodiments, the one of the first and second surfaces of the spreader block is recessed to form a pocket in which the uninflated balloon resides. The pocket protects the uninflated balloon during its insertion into the disc space.

In some embodiments, the distractor of FIGS. 14a-15b is the distal end portion of an instrument and is used to distract and clear the disc space. It is then removed from the disc space.

In some embodiments, the distractor of FIGS. 14a-15b is the distal end portion of an implant and may be filled with a strut material to support the disc space during fusion.

Figure 16A:
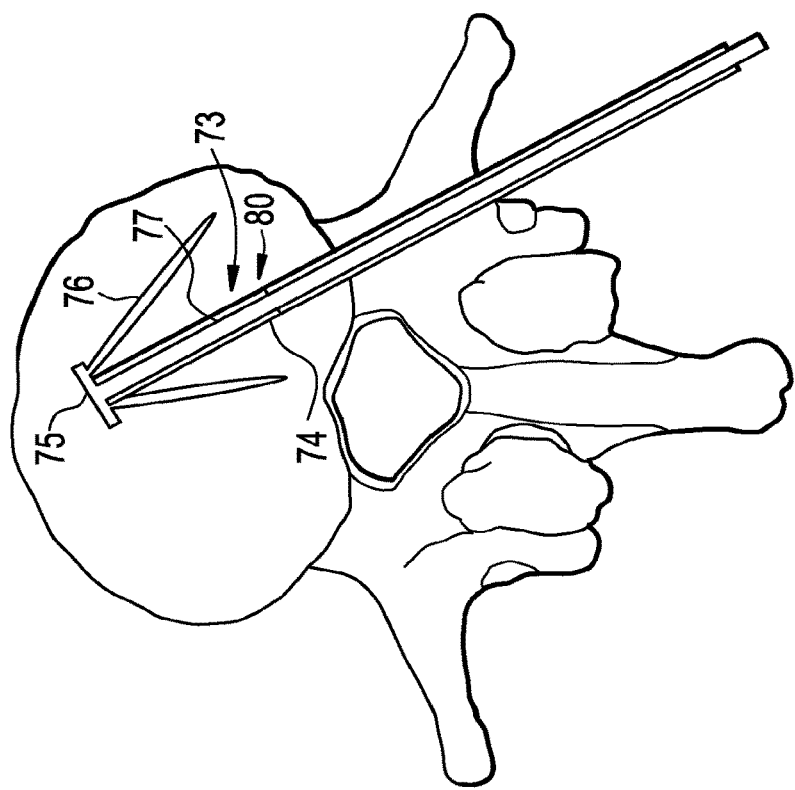
FIG. 16a-17b discloses an integrated distractor, wherein the balloon resides within a slot in the spreader.
Figure 16B:
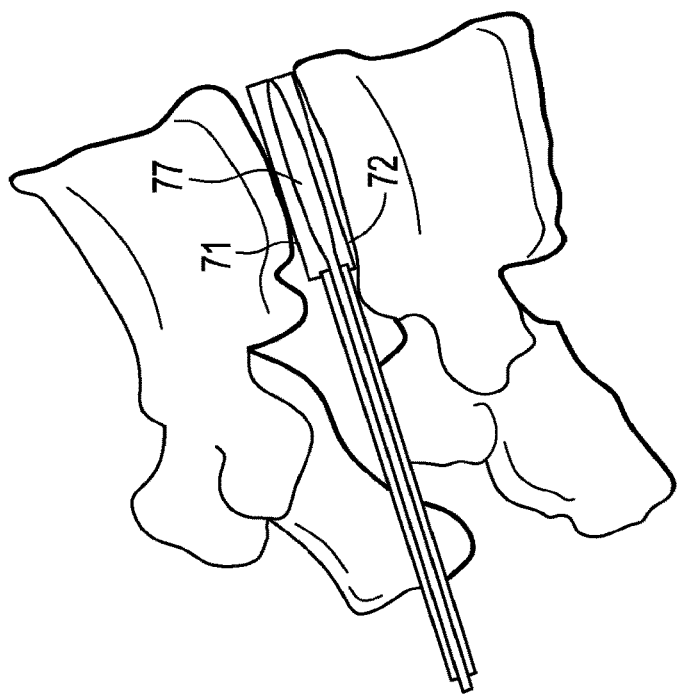
Figure 17B:
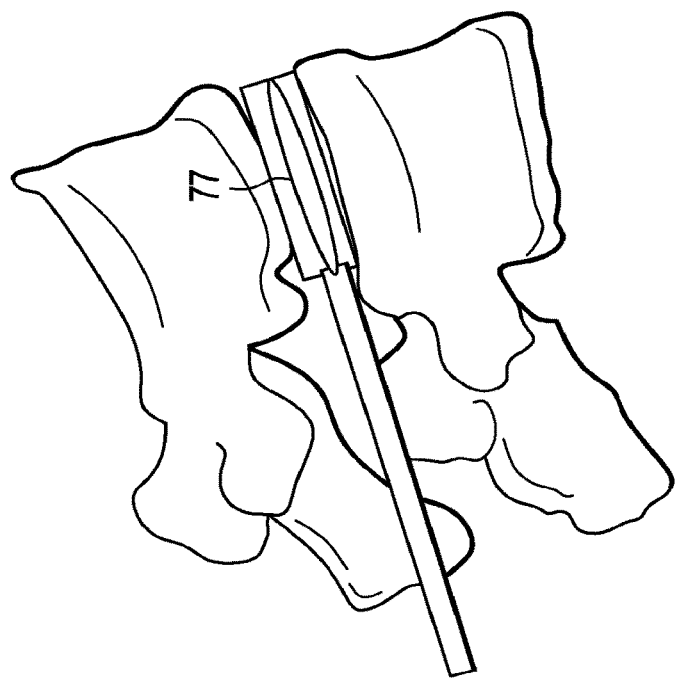
Figure 17A:
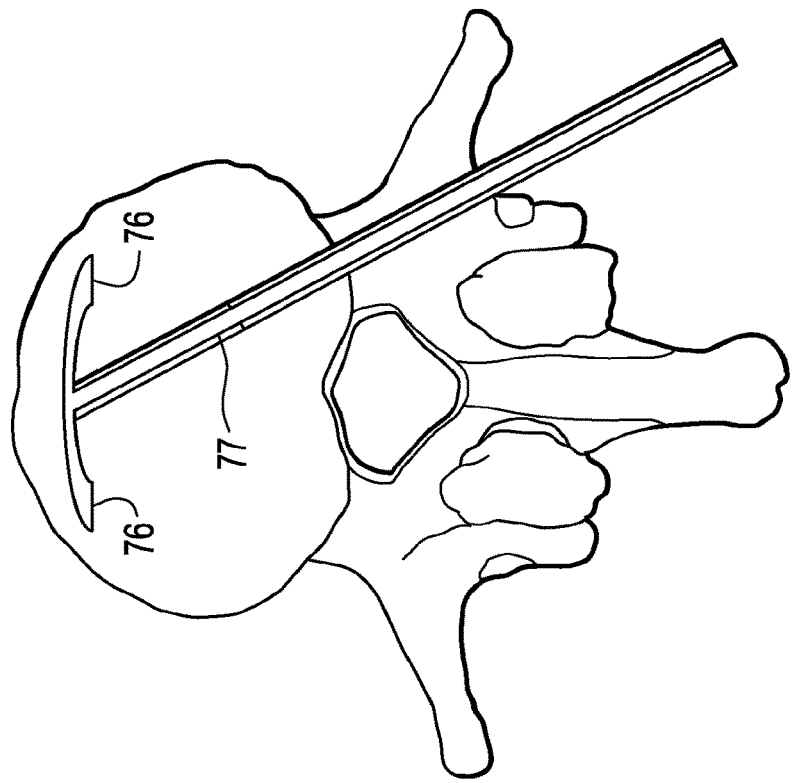

In another embodiment of the present invention, and now referring to FIGS. 16a-17b, there is provided a method of treating a disc, comprising the steps of:
- a) providing an insertion device comprising i) a spreader block 80 having a height defined by first 71 and second 72 surfaces, a width defined by third 73 and fourth 74 surfaces, and a slot extending between the third and fourth surfaces, wherein the height is less than the width, and ii) an uninflated balloon 75 having a proximal portion 77 within the slot and a distal portion 76 extending outside the slot;
- b) inserting the spreader block into the disc space so that the first and second surfaces thereof contact the opposed vertebral body endplates,
- c) rotating the spreader block in the disc space so that the third and fourth surfaces thereof contact the opposed vertebral body endplates, and
- d) inflating the balloon as the third and fourth surfaces of the spreader block contact the opposed vertebral body endplates.

This method provides for use of an integrated distractor, wherein the balloon resides within a slot in the distractor.

Also in accordance with the present invention, and still referring to FIGS. 16a-17b, there is provided a distractor comprising:
- i) a spreader block having a height defined by first and second surfaces, a width defined by third and fourth surfaces, and a slot extending between the third and fourth surfaces, wherein the height is less than the width, and
- ii) an uninflated balloon having a proximal portion within the slot and a distal portion extending outside the slot;

In some embodiments, the distal portion of the balloon forms a shape when inflated that runs substantially transverse to the spreader block. Preferably, such a shape is a banana shape.

In some embodiments, the distractor of FIGS. 16a-17b is the distal end portion of an instrument and is used to distract and clear the disc space. It is then removed from the disc space.

In some embodiments, the distractor of FIGS. 16a-17b is the distal end portion of an implant and may be filled with a strut material to support the disc space during fusion.

Figure 18B:
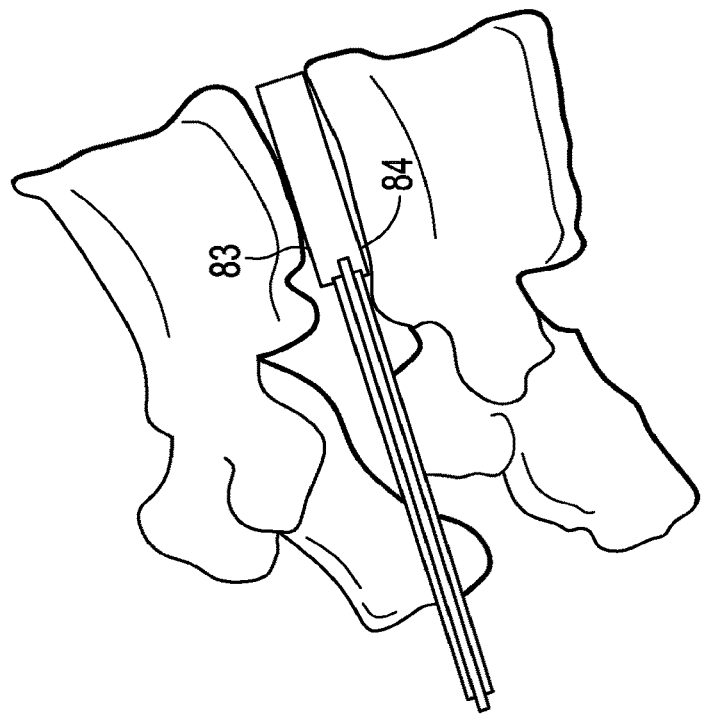
FIG. 18a-19b discloses an integrated distractor, wherein the balloon resides within a slot in the non-rotating distractor.
Figure 18A:
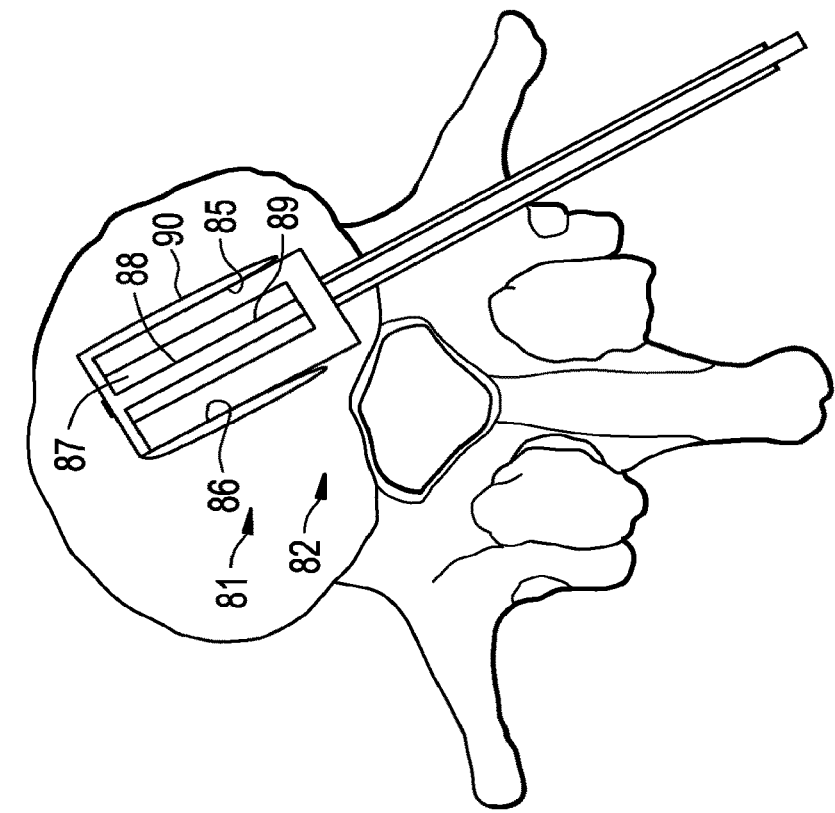
Figure 19B:
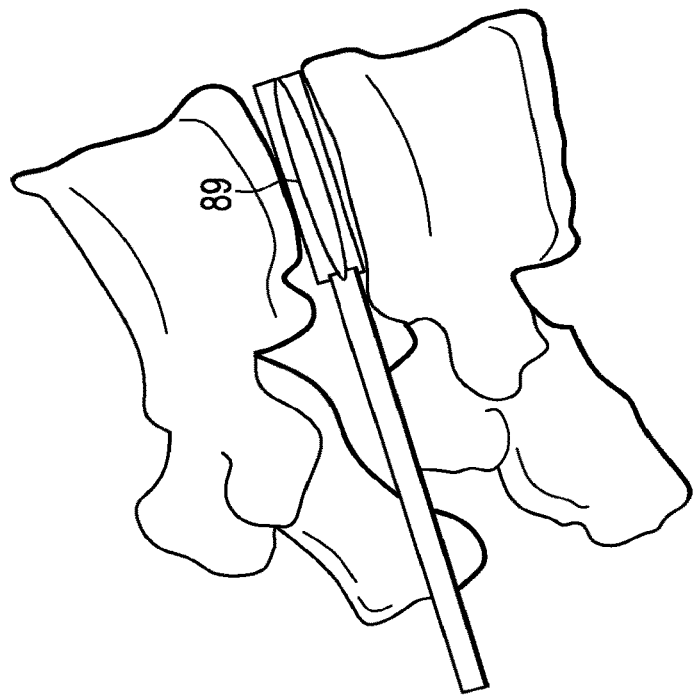
Figure 19A:
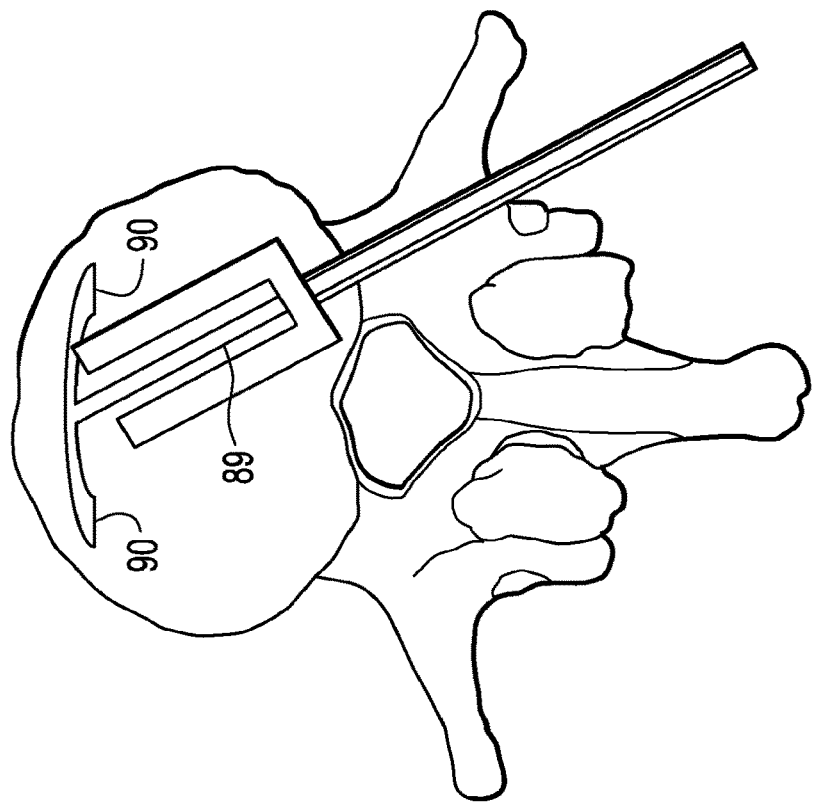

In another embodiment of the present invention, and now referring to FIGS. 18a-19b, there is provided a method of treating a disc, comprising the steps of:
- a) providing an insertion device 81 comprising i) a spreader block 82 having a height defined by first 83 and second 84 surfaces, a width defined by third 85 and fourth 86 surfaces, and a slot 87 extending between the first and second surfaces, and ii) an uninflated balloon 88 having a proximal portion 89 within the slot and a distal portion 90 extending outside the slot;
- b) inserting the spreader block into the disc space so that the first and second surfaces thereof contact the opposed vertebral body endplates,
- c) inflating the balloon as the first and second surfaces of the spreader block contact the opposed vertebral body endplates.

FIG. 18a-19b discloses an integrated distractor, wherein the balloon resides within a slot in the non-rotating distractor.

Also in accordance with the present invention, and still referring to FIGS. 18a-19b, there is provided a distractor comprising:
- i) a spreader block having a height defined by first and second surfaces, a width defined by third and fourth surfaces, and a slot extending between the first and second surfaces, and
- ii) an uninflated balloon having a proximal portion within the slot and a distal portion extending outside the slot.

In some embodiments, the distal portion of the balloon forms a shape when inflated that runs substantially transverse to the spreader block. Preferably, such a shape is a banana shape.

In some embodiments, the distractor of FIGS. 18a-19b is the distal end portion of an instrument and is used to distract and clear the disc space. It is then removed from the disc space.

In some embodiments, the distractor of FIGS. 18a-19b is the distal end portion of an implant and may be filled with a strut material to support the disc space during fusion.

Figure 20B:
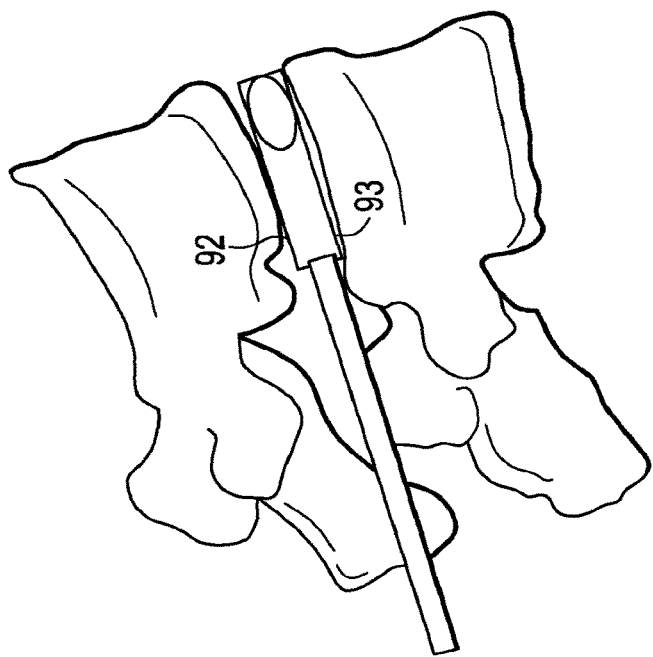
FIG. 20a-21b discloses an integrated distractor having deployable spreader block portions.
Figure 20A:
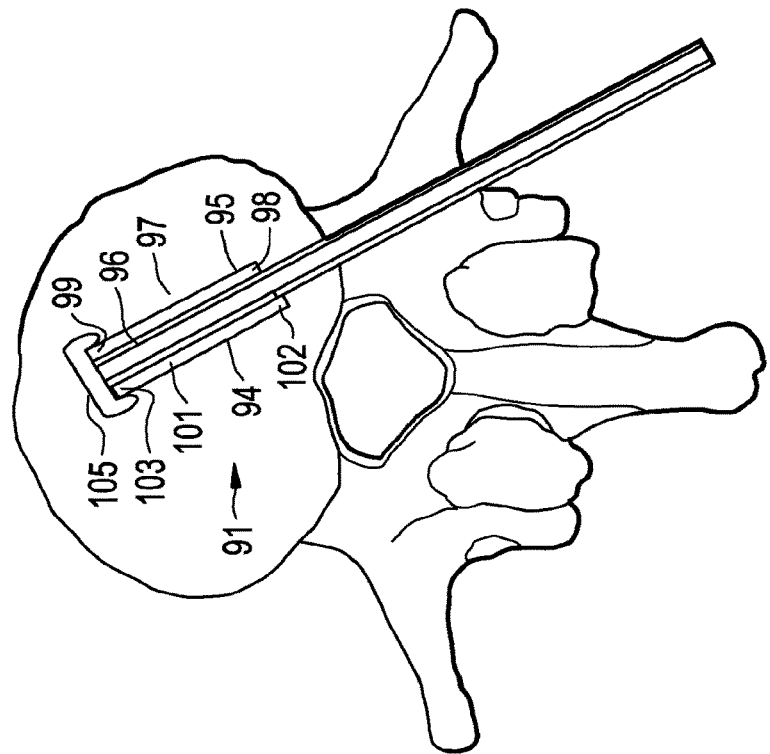
Figure 21B:
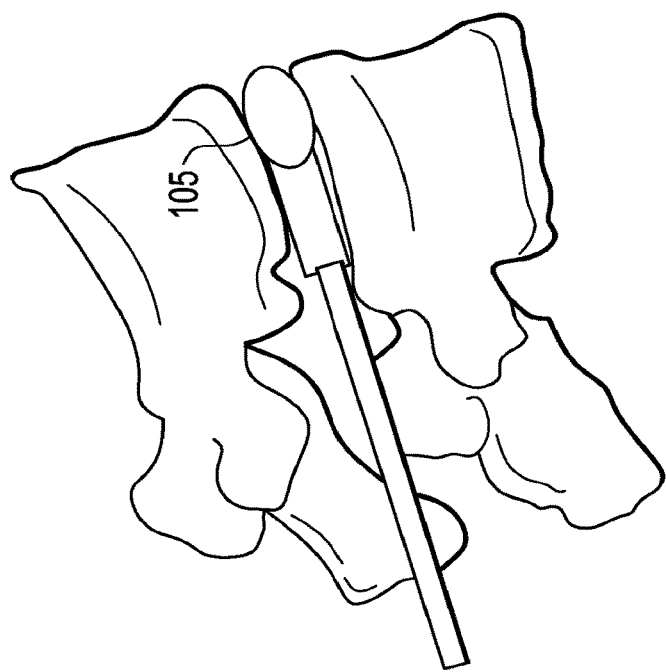
Figure 21A:
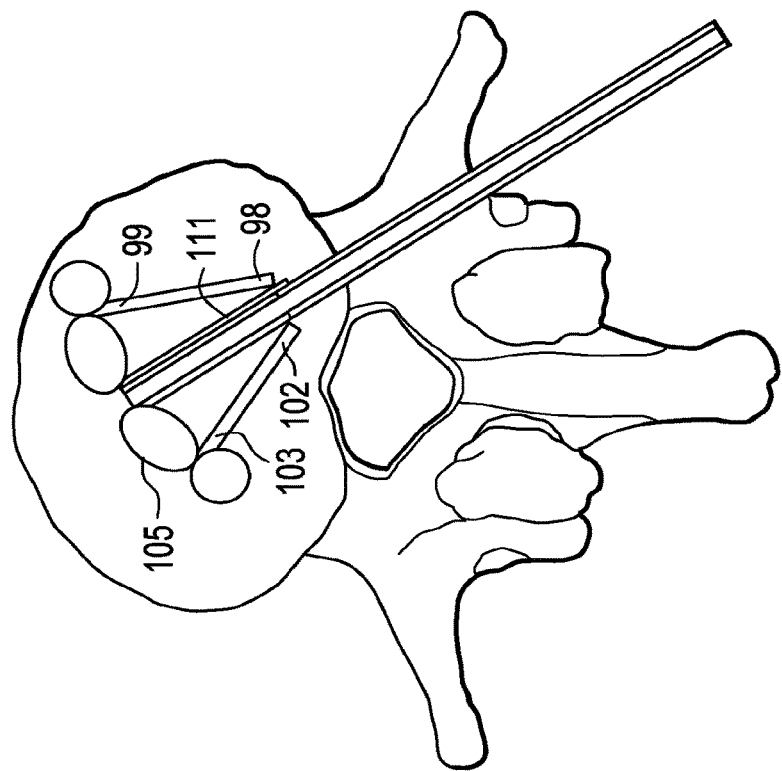

In another embodiment of the present invention, and now referring to FIGS. 20a-21b, there is provided a method of treating a disc, comprising the steps of:
- a) providing a distractor comprising i) a spreader block 91 having a height defined by first 92 and second 93 surfaces, a width defined by third 94 and fourth 95 surfaces, and a slot 96 extending between the first and second surfaces, ii) a first deployable arm 97 having a proximal portion 98 hinged at a proximal end portion 111 of the spreader block on the third surface thereof and a distal portion 99, iii) a second deployable arm 101 having a proximal portion 102 hinged at the proximal end portion of the spreader block on the fourth surface thereof and a distal portion 103, and iv) an uninflated balloon 105 extending from the slot and attached to the distal portions of each deployable arm;
- b) inserting the spreader block into the disc space so that the first and second surfaces thereof contact the opposed vertebral body endplates, c) inflating the balloon as the first and second surfaces of the spreader block contact the opposed vertebral body endplates.

In this embodiment, the balloon is contained within a sectioned spreader block having deployable spreader block portions.

Also in accordance with the present invention, and still referring to FIGS. 20a-21b, there is provided a distractor comprising:
i) a spreader block having a height defined by first and second surfaces, a width defined by third and fourth surfaces, and a slot extending between the first and second surfaces,
ii) at least one arm having a proximal portion hinged at the proximal end portion of the spreader block on the third surface thereof and a distal portion,
iii) an uninflated balloon extending from the slot and attached to the distal portions of the deployable arm.

In some embodiments, the balloon forms a shape when inflated that runs substantially transverse to the spreader block. Preferably, such a shape is a banana shape.

In some embodiments, the distractor of FIGS. 20a-21b is the distal end portion of an instrument and is used to distract and clear the disc space. It is then removed from the disc space.

In some embodiments, the distractor of FIGS. 20a-21b is the distal end portion of an implant and may be filled with a strut material to support the disc space during fusion.

The device may be made of materials typically selected for use in surgical instruments. Preferably, the entire device is sterile.

When placed in-situ (and in some instances, after curing), the flowable material that fills the balloon preferably replaces as least a portion of the natural function of the nucleus fibrosis. Accordingly, in preferred embodiments, the flowable material is a nucleus pulposus replacement. The flowable materials are preferably selected from the group consisting of liquids, gels (such as hydrogels, such as PVA-based hydrogels), and solid materials that are sufficiently morselized to flow under pressure. Typically, the liquid flowable material cures in-situ. The flowable material may cure in-situ to create a stiff material (such as polyurethane), or a relatively pliant material (such as silicone).

In other embodiments, the balloon may also be filled in accordance with the methods and materials recited in US Published Patent Application 2004/0230309, filed Feb. 13, 2004 entitled "In-situ formed intervertebral fusion device and method", the specification of which is incorporated by reference in its entirety.

We claim:

1. A surgical method comprising:
inserting an outer cannula into a disc space, the outer cannula having an inner elongate member slidably disposed therein;
longitudinally sliding the inner elongate member relative to the outer cannula to expose a distal end portion of the inner elongate member within the disc space and thereby cause the distal end portion of the inner elongate member to revert to a curved memorized shape within the disc space, whereby a distal-facing end surface of the distal end portion substantially abuts a sidewall of a proximal portion of the inner elongate member; and
delivering a fusion material through a delivery hole formed through a sidewall of the inner elongate member to fill an interior of the curved memorized shape, the inner elongate member containing the fusion material within the disc space in a radial plane but not in a cephalad-caudal direction.

2. The method of claim 1, wherein the proximal portion of the inner elongate member is substantially straight.

3. The method of claim 1, wherein the fusion material is delivered to an interior of a balloon.

4. The method of claim 1, wherein the inner elongate member has a rectangular transverse cross-section.

5. The method of claim 1, wherein, when the distal-facing end surface of the distal end portion substantially abuts the sidewall of the proximal portion of the inner elongate member, the proximal portion of the inner elongate member is adjacent to a distal end of the outer cannula.

6. The method of claim 1, wherein the curved memorized shape is annular.

7. The method of claim 1, wherein an upper surface of the inner elongate member lies in a single plane when the inner elongate member is in the curved memorized shape.

8. The method of claim 1, wherein the fusion material comprises one or more of a bone cement, an osteoinductive cement, bone particles, a bone substitute, and a growth factor.

9. The method of claim 1, wherein the inner elongate member forms a substantially full ring when reverted to the curved memorized shape.

10. A surgical method comprising:
delivering an inner elongate member to a disc space in a substantially straight configuration, the inner elongate member comprising a shape memory material;
forming the inner elongate member into a curved memorized shape within the disc space, the inner elongate member in the curved memorized shape comprising a terminal distal end face that faces a sidewall of a proximal portion of the inner elongate member; and
delivering a fusion material through a delivery hole formed through a sidewall of the inner elongate member to fill an interior of the curved memorized shape, the inner elongate member containing the fusion material within the disc space in a radial plane.

11. The method of claim 10, wherein the proximal portion of the inner elongate member is substantially straight.

12. The method of claim 10, wherein the fusion material is delivered to an interior of a balloon.

13. The method of claim 10, wherein the inner elongate member has a rectangular transverse cross-section.

14. The method of claim 10, wherein, when the terminal distal end face faces the sidewall of the proximal portion of the inner elongate member, the proximal portion of the inner elongate member is adjacent to a distal end of an outer cannula in which a portion of the inner elongate member is disposed.

15. The method of claim 10, wherein the curved memorized shape is annular.

16. The method of claim 10, wherein an upper surface of the inner elongate member lies in a single plane when the inner elongate member is in the curved memorized shape.

17. The method of claim 10, wherein the fusion material comprises one or more of a bone cement, an osteoinductive cement, bone particles, a bone substitute, and a growth factor.

18. The method of claim 10, wherein the inner elongate member forms a substantially full ring when in the curved memorized shape.

19. The method of claim 10, wherein the terminal distal end face of the inner elongate member contacts the proximal portion of the inner elongate member when the inner elongate member is in the curved memorized shape.

\* \* \* \* \*